United States Patent
Perez et al.

(10) Patent No.: US 7,235,083 B1
(45) Date of Patent: Jun. 26, 2007

(54) METHODS AND DEVICES FOR AIDING IN SITU ASSEMBLY OF REPAIR DEVICES

(75) Inventors: Juan I. Perez, Sunnyvale, CA (US); Masoud Molaei, Fremont, CA (US); Shahrokh R. Farahani, Danville, CA (US); Michael F. Wei, Menlo Park, CA (US); Shuji Uemura, San Francisco, CA (US); Natalie Fawzi, Belmont, CA (US)

(73) Assignee: Endovascular Technologies, Inc., Santa Clara, CA (US)

( * ) Notice: Subject to any disclaimer, the term of this patent is extended or adjusted under 35 U.S.C. 154(b) by 598 days.

(21) Appl. No.: 10/661,009

(22) Filed: Sep. 10, 2003

(51) Int. Cl.
*A61F 2/84* (2006.01)
*A61M 25/01* (2006.01)
*A61M 25/10* (2006.01)

(52) U.S. Cl. .............. 606/108; 623/1.11; 606/194; 604/164.09

(58) Field of Classification Search .............. 606/108, 606/113, 191, 194, 200; 623/1.11, 1.35; 604/164.09, 96; 600/104
See application file for complete search history.

(56) References Cited

U.S. PATENT DOCUMENTS

| | | | |
|---|---|---|---|
| 3,657,744 A | 4/1972 | Ersek | |
| 4,061,134 A | 12/1977 | Samuels et al. | |
| 4,108,161 A | 8/1978 | Samuels et al. | |
| 4,140,126 A | 2/1979 | Choudhury | |
| 4,214,587 A | 7/1980 | Sakura, Jr. | |
| 4,577,631 A | 3/1986 | Kreamer | |
| 4,617,932 A | 10/1986 | Kornberg | |
| 4,728,328 A | 3/1988 | Hughes et al. | |
| 4,732,152 A | 3/1988 | Wallsten et al. | |
| 4,739,762 A | 4/1988 | Palmaz | |
| 4,787,899 A | 11/1988 | Lazarus | |
| 4,793,348 A | 12/1988 | Palmaz | |
| 4,795,458 A | 1/1989 | Regan | |
| 4,830,003 A | 5/1989 | Wolff et al. | |
| 4,872,874 A | 10/1989 | Taheri | |
| 4,969,896 A | 11/1990 | Shors | |
| 4,994,071 A | 2/1991 | MacGregor | |
| 5,026,377 A | 6/1991 | Burton et al. | |
| 5,047,050 A | 9/1991 | Arpesani | |
| 5,064,435 A | 11/1991 | Porter | |
| 5,078,726 A | 1/1992 | Kreamer | |
| 5,104,399 A | 4/1992 | Lazarus | |
| 5,122,154 A | 6/1992 | Rhodes | |

(Continued)

FOREIGN PATENT DOCUMENTS

DE 9319267 4/1994

(Continued)

OTHER PUBLICATIONS

Marcade et al., U.S. Appl. No. 09/637,505, filed Aug. 11, 2000.

(Continued)

*Primary Examiner*—Julian W. Woo
*Assistant Examiner*—Sarah Webb
(74) *Attorney, Agent, or Firm*—Fulwider Patton LLP

(57) ABSTRACT

Methods and devices for facilitating the repair of vasculature. The methods and devices described accomplish engagement of components employed during in situ assembly of repair devices.

17 Claims, 27 Drawing Sheets

U.S. PATENT DOCUMENTS

| | | | |
|---|---|---|---|
| 5,123,917 A | 6/1992 | Lee | |
| 5,192,297 A | 3/1993 | Hull | |
| 5,201,757 A | 4/1993 | Heyn et al. | |
| 5,219,355 A | 6/1993 | Parodi et al. | |
| 5,275,622 A | 1/1994 | Lazarus et al. | |
| 5,282,824 A | 2/1994 | Gianturco | |
| 5,292,331 A | 3/1994 | Boneau | |
| 5,316,023 A | 5/1994 | Palmaz et al. | |
| 5,360,443 A | 11/1994 | Barone et al. | |
| 5,387,235 A | 2/1995 | Chuter | |
| 5,395,334 A | 3/1995 | Keith et al. | |
| 5,397,345 A | 3/1995 | Lazarus | |
| 5,562,724 A | 10/1996 | Vorwerk et al. | |
| 5,575,817 A | 11/1996 | Martin | |
| 5,628,783 A | 5/1997 | Quiachon et al. | |
| 5,628,788 A | 5/1997 | Pinchuk | |
| 5,632,772 A | 5/1997 | Alcime et al. | |
| 5,639,278 A | 6/1997 | Dereume et al. | |
| 5,653,743 A | 8/1997 | Martin | |
| 5,676,696 A | 10/1997 | Marcade | |
| 5,683,449 A | 11/1997 | Marcade | |
| 5,683,450 A | 11/1997 | Goicoechea et al. | |
| 5,693,083 A | 12/1997 | Baker et al. | |
| 5,693,084 A | 12/1997 | Chuter | |
| 5,716,365 A | 2/1998 | Goicoechea et al. | |
| 5,718,724 A | 2/1998 | Goicoechea et al. | |
| 5,723,004 A | 3/1998 | Dereume et al. | |
| 5,741,325 A | 4/1998 | Chaikof et al. | |
| 5,755,769 A | 5/1998 | Richard et al. | |
| 5,769,885 A | 6/1998 | Quiachon et al. | |
| 5,776,180 A | 7/1998 | Goicoechea et al. | |
| 5,800,508 A | 9/1998 | Goicoechea et al. | |
| 5,824,037 A | 10/1998 | Fogarty et al. | |
| 5,824,055 A | 10/1998 | Spiridigliozzi et al. | |
| 5,855,598 A | 1/1999 | Pinchuk | |
| 5,916,263 A | 6/1999 | Goicoechea et al. | |
| 5,938,696 A | 8/1999 | Goicoechea et al. | |
| 5,993,481 A | 11/1999 | Marcade et al. | |
| 6,015,431 A | 1/2000 | Thornton et al. | |
| 6,051,020 A | 4/2000 | Goicoechea et al. | |
| 6,071,233 A * | 6/2000 | Ishikawa et al. | 600/104 |
| 6,099,558 A | 8/2000 | White et al. | |
| 6,102,938 A | 8/2000 | Evans et al. | |
| 6,117,167 A | 9/2000 | Goicoechea et al. | |
| 6,123,722 A | 9/2000 | Fogarty et al. | |
| 6,149,682 A | 11/2000 | Frid | |
| 6,165,195 A * | 12/2000 | Wilson et al. | 606/108 |
| 6,280,432 B1 * | 8/2001 | Turovskiy et al. | 604/164.09 |
| 6,325,823 B1 | 12/2001 | Horzewski et al. | |
| 6,395,022 B1 | 5/2002 | Piplani et al. | |
| 6,409,756 B1 | 6/2002 | Murphy | |
| 6,592,615 B1 | 7/2003 | Marcade et al. | |
| 2005/0234297 A1 * | 10/2005 | Devierre et al. | 600/104 |

FOREIGN PATENT DOCUMENTS

| | | |
|---|---|---|
| EP | 0 461 791 | 12/1991 |
| EP | 0 508 473 | 10/1992 |
| EP | 0 539 237 | 4/1993 |
| EP | 0 637 454 | 2/1995 |
| EP | 0 646 365 | 4/1995 |
| FR | 2 678 508 | 1/1993 |
| FR | 2 748 197 | 11/1997 |
| SU | 1217402 | 3/1986 |
| SU | 1318235 | 6/1987 |
| SU | 1389778 | 4/1988 |
| SU | 1457921 | 2/1989 |
| SU | 1482714 | 5/1989 |
| WO | WO 84/02266 | 6/1984 |
| WO | WO 95/01761 | 1/1995 |
| WO | WO 95/16406 | 6/1995 |

OTHER PUBLICATIONS

Marcade et al., U.S. Appl. No. 09/777,274, filed Feb. 2, 2001.

Chuter, et al., "Transfemoral Endovascular Aortic Graft Placement," Journal of Vascular Surgery, vol. 18, No. 2, Aug. 1993, pp. 185-197.

Parodi, et al., "Transfemoral Intraluminal, Graft Implantation for Abdominal Aortic Aneurysms," Annals of Vascular Surgery, vol. 5, No. 6, 1991, p. 491-499.

Criado, et al., "Transluminal Recanalization, Angioplasty and Stenting in Endovascular Surgery: Techniques and Applications," from Greenhalgh, Vascular and Endovascular Surgical Techniques, 3$^{rd}$ Edition, 1994, pp. 49-70.

Marin et al., "Endoluminal Stented Graft Aorto-Bifemoral Reconstruction," from Greenhalgh, Vascular and Endovascular Surgcial Techniques, 3$^{rd}$ Edition, 1994, pp. 100-104.

May et al., "Transluminal Placement of a Prosthetic Graft-Stent Device for Treatment of Subclavian Artery Aneurysm," Journal of Vascular Surgery, vol. 18, No. 6, Dec. 1993, pp. 1056-1059.

Chuter, T., "Bifurcated Endovascular Graft Insertion for Abdominal Aortic Aneurysm" from Greenhalgh, Vascular and Endovascular Surgical Techniques, 3$^{rd}$ Edition, 1994, pp. 92-99.

Moore, W.S., "Transfemoral Endovascular Repair of Abdominal Aortic Aneurysm Using the Endovascular Graft System Device," from Greenhalgh, Vascular and Endovascular Surgical Techniques, 3$^{rd}$ Edition, 1994, pp. 78-91.

* cited by examiner

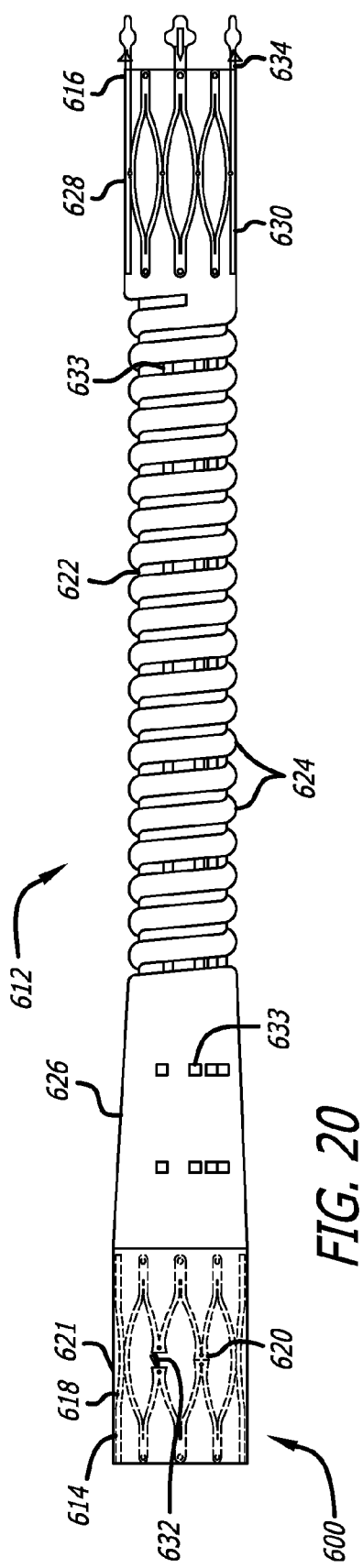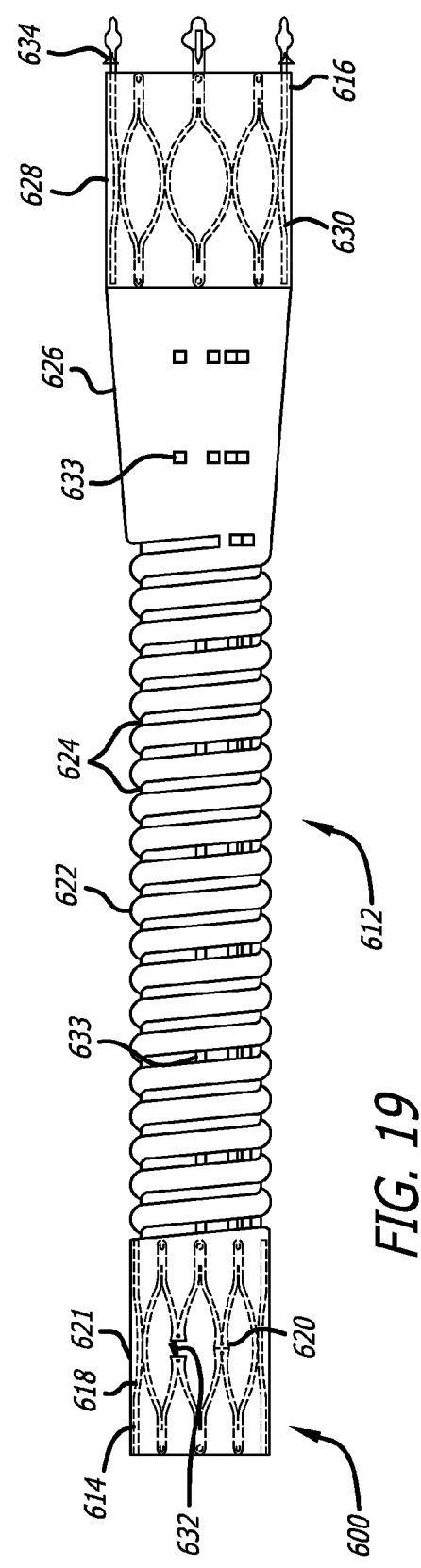

METHODS AND DEVICES FOR AIDING IN SITU ASSEMBLY OF REPAIR DEVICES

BACKGROUND OF THE INVENTION

The present invention relates generally to vasculature repair and more particularly to methods and devices for accomplishing in situ assembly of a repair device for treating abdominal aortic aneurysms.

It is well established that various fluid conducting body or corporeal lumens, such as veins and arteries, may deteriorate or suffer trauma so that repair is necessary. For example, various types of aneurysms or other deteriorative diseases may affect the ability of the lumen to conduct fluids and, in turn, may be life threatening. In some cases, the damage to the lumen is repairable only with the use of prosthesis such as an artificial vessel or graft.

For repair of vital lumens such as the aorta, surgical repair is significantly life threatening or subject to significant morbidity. Surgical techniques known in the art involve major surgery in which a graft resembling the natural vessel is spliced into the diseased or obstructed section of the natural vessel. Known procedures include surgically removing the damaged or diseased portion of the vessel and inserting an artificial or donor graft portion inserted and stitched to the ends of the vessel which were created by the removal of the diseased portion. More recently, devices have been developed for treating diseased vasculature through intraluminal repair. Rather than removing the diseased portion of the vasculature, the art has taught bypassing the diseased portion with a prosthesis and implanting the prosthesis within the vasculature. An intra arterial prosthesis of this type has two components: a flexible conduit, the graft, and the expandable framework, the stent (or stents). Such a prosthesis is called an endovascular graft.

It has been found that many abdominal aortic aneurysms extend to the aortic bifurcation. Accordingly, a majority of cases of endovascular aneurysm repair employ a graft having a bifurcated shape with a trunk portion and two limbs, each limb extending into separate branches of vasculature. Currently available bifurcated endovascular grafts fall into two categories. One category of grafts are those in which a preformed graft is inserted whole into the arterial system and manipulated into position about the area to be treated. This is a unibody graft. The other category of endovascular grafts are those in which a graft is assembled in-situ from two or more endovascular graft components. This latter endovascular graft is referred to as a modular endovascular graft. Because a modular endovascular graft facilitates greater versatility of matching the individual components to the dimensions of the patient's anatomy, the art has taught the use of modular endovascular grafts in order to minimize difficulties encountered with insertion of the devices into vasculature and sizing to the patient's vasculature.

Although the use of modular endovascular grafts minimize some of the difficulties, there are still drawbacks associated with the current methods. Where it is desirable to repair vasculature with a repair device that is assembled in situ, it can be difficult to accomplish mating the various components of the repair device. For example, it can be difficult to access an inferior opening of a bifurcated graft or repair device. That is, components that are designed to mate with contralateral limbs of a graft or repair device are sometimes difficult to align with a contralateral opening. Remote imaging techniques such as fluoroscopy provide a two dimensional display of components residing in a three-dimensional environment. Thus, gaining access to inferior openings can be a challenge. Often the challenge involves attempting to thread a guidewire through a contralateral limb opening of a repair device which later provides a track for delivering additional components designed to mate with the repair device. This challenge can also apply to any component which terminates in an opening having a smaller cross-section than the anatomy, such as a repair device with a target opening residing in an aneurysm.

Accordingly, there exists a need for methods or devices which overcome or tend to minimize the challenges associated with assembling components that have cross-sections less than the vasculature being repaired or where two dimensional imaging is found to be lacking. The present invention addresses these and other needs.

SUMMARY OF THE INVENTION

Briefly and in general terms, the present invention relates to methods and devices for use in the repair of vasculature and more particularly for use in connection with the in situ assembly of a modular endovascular graft. In one or more aspects, the present invention is directed at facilitating the snaring of a guidewire placed within vasculature. In other aspects, the present invention is concerned with accomplishing the advancement of a guidewire through an opening of an endovascular graft or repair device.

In one embodiment, there is provided a main catheter carrying a first modular component and being equipped with a snare target wire having a snare target ball formed at a terminal end thereof. A soft magnet snare is further provided and is designed to engage the snare target ball to facilitate placement of a guidewire in the opening of the first endovascular graft component to then accomplish placing a second modular component in contact with the first component. In an alternative embodiment, the snare target ball is contemplated to be ferromagnetic to further facilitate the engagement of the snare target ball and the snare. Radiopacity of the snare target ball is highly beneficial.

In another embodiment, advancement of a guidewire to a specific location within the first endovascular component or patient's vasculature is accomplished by creating retrograde blood flow within a vessel. A guidewire configured with a balloon or other retractable occlusion structure is advanced within vasculature to a target site. The occlusion structure is expanded to create a pressure gradient at the target site. The occlusion structure is then retracted or compressed and the guidewire is allowed to be advanced further within the vasculature through the aid of the retrograde flow created.

In a further embodiment, a guidewire is equipped with structure which provides both physical or visual feedback (through remote imaging techniques) and steering through blood flow. The guidewire tip includes atraumatic fins/rudders or wind socks which act to aid in progressing the guidewire straight up a course of flow of blood. Any misdirection of the guidewire tip results in a dramatic lateral change in position of the tip.

In yet another embodiment, the tip of a guidewire can be coiled into a flat spiral or a spherical or conical shape to thereby provide an enlarged structure to aim at a target site. In this embodiment, a proximal end of the guidewire can be manipulated to cause the enlarged terminal end of the guidewire to become straightened or reduced in dimension for insertion within a target lumen or opening.

In another embodiment, a temporary tunnel or pathway is created within vasculature by a balloon catheter or tampon structure through which a guidewire is advanced to a target site. By minimizing the area through which the guidewire can move laterally, there can be a more efficient placement of the guidewire at the target site.

In another embodiment, a snare assembly is provided with a catheter snare for grabbing a main catheter during an implantation procedure. The snare assembly additionally includes a dual lumen or peelaway structure housing a contralateral guidewire. In a disclosed method, after engaging the main catheter with the catheter snare, the snare assembly is aligned with a marker attached to the target site. The contralateral guidewire is then advanced to the target site and thereafter, the snare is disengaged from the main catheter.

In another embodiment, a snare catheter is included in the main catheter and a swiveling guide is provided to direct the snare catheter over the bifurcation of the repair device and out the contralateral port. In a disclosed method, the snare catheter is utilized to capture a guidewire inserted into the contralateral vessel and pull the guidewire into the main body of the repair device.

Other features and advantages of the present invention will become apparent from the following detailed description, taken in conjunction with the accompanying drawings, which illustrate, by way of example, the principles of the invention.

BRIEF DESCRIPTION OF THE DRAWINGS

FIG. 19 is a side elevational view, depicting a crimped tubular graft leg having an inferior end with a larger diameter than a superior end;

FIG. 20 is a side elevational view, depicting a crimped tubular graft leg having an inferior end with a smaller diameter than a superior end;

DETAILED DESCRIPTION OF THE PREFERRED EMBODIMENTS

Figure 1:
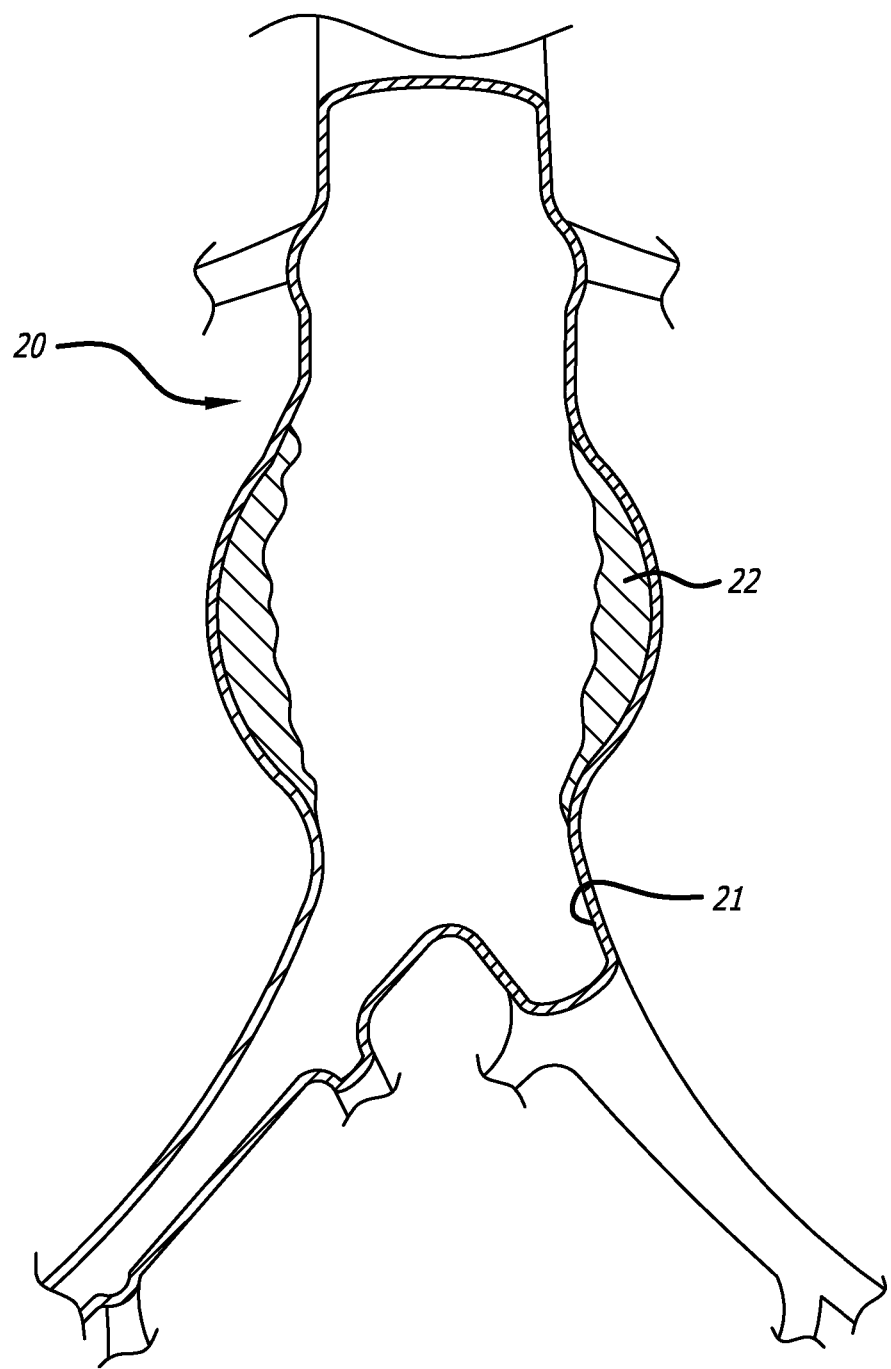
FIG. 1 is a cutaway view, depicting a typical repair site within vasculature.

As shown in the drawings, which are included for illustration and not by way of limitation, the present inventions are embodied in methods and devices for facilitating in situ assembly of modular repair devices. The disclosed methods and devices address problems associated with conventional modular repair devices and catheters employed to deliver the repair devices within vasculature. The disclosed inventions can be employed to deliver components of any modular repair devices within various portions of a patient's vasculature. As will be developed below, the present inventions are particularly useful in the assembly of modular endovascular grafts within the aorta 20 to repair an aneurysm 22 (See FIG. 1) wherein the problem is that a small opening 66 (See FIG. 3), in the first modular component 60 lies within a large cavity 23 in the body just above a relatively small diameter vessel 21 that has a lot of bends which makes it difficult to pass a conventional guidewire through the vessel across a portion of the large cavity and into the small opening 66 (see FIG. 3).

Figure 2:
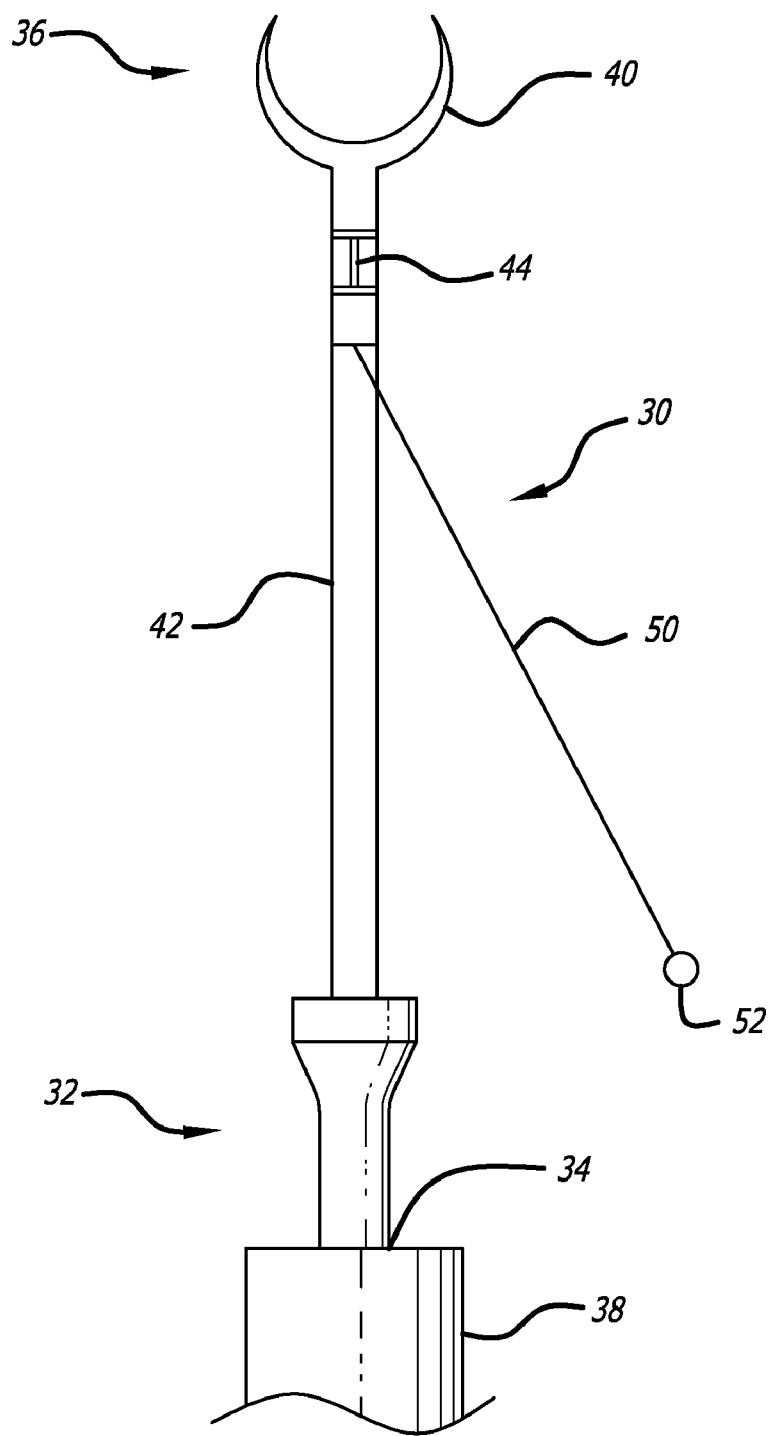
FIG. 2 is a partial side view, depicting a catheter equipped with a snare target.

Referring now to FIGS. 2–7, a device and a method are described for accomplishing the cannulating of a contralateral opening of a modular abdominal aortic aneurysm endovascular graft implant. As stated, however, the disclosed system can be used anywhere in a patient's vasculature for the assembly of any repair device by altering the dimensions thereof. As shown in FIG. 2, a repair system 30 includes an elongate main catheter 32 having an inferior portion (not shown) and a superior portion 36. The repair system 30 has a tubular jacket 38 which is sized to slide over the main catheter 32. The jacket 38 (shown retracted) is used to provide the system 30 with a profile suitable for advancement within vasculature. At a repair site, the jacket is retracted to expose the superior portion 36 of the main catheter 32, the various components thereof, and a first modular component 60 (shown deployed in FIG. 3).

The superior portion 36 of the main catheter 32 includes a terminal end configured with a tapered nosecone 41 and a generally blunt jacket guard 40 which mates with the jacket 38 when the system 30 is assembled for advancement through vasculature. The jacket guard 40, tapered nosecone 41 and jacket 38 define an atraumatic superior end. The main catheter 32 further includes a repair device or modular endovascular graft mounting or receiving portion 42 as well as a release wire port 44. The release wire port 44 is designed to provide an opening for a release wire (not shown) that can be configured to maintain a repair device on the main catheter 32 in a compressed condition then subsequently pulled to allow the repair device to expand. The system 30 can also be equipped with an expandable member such as a balloon.

Figure 3:
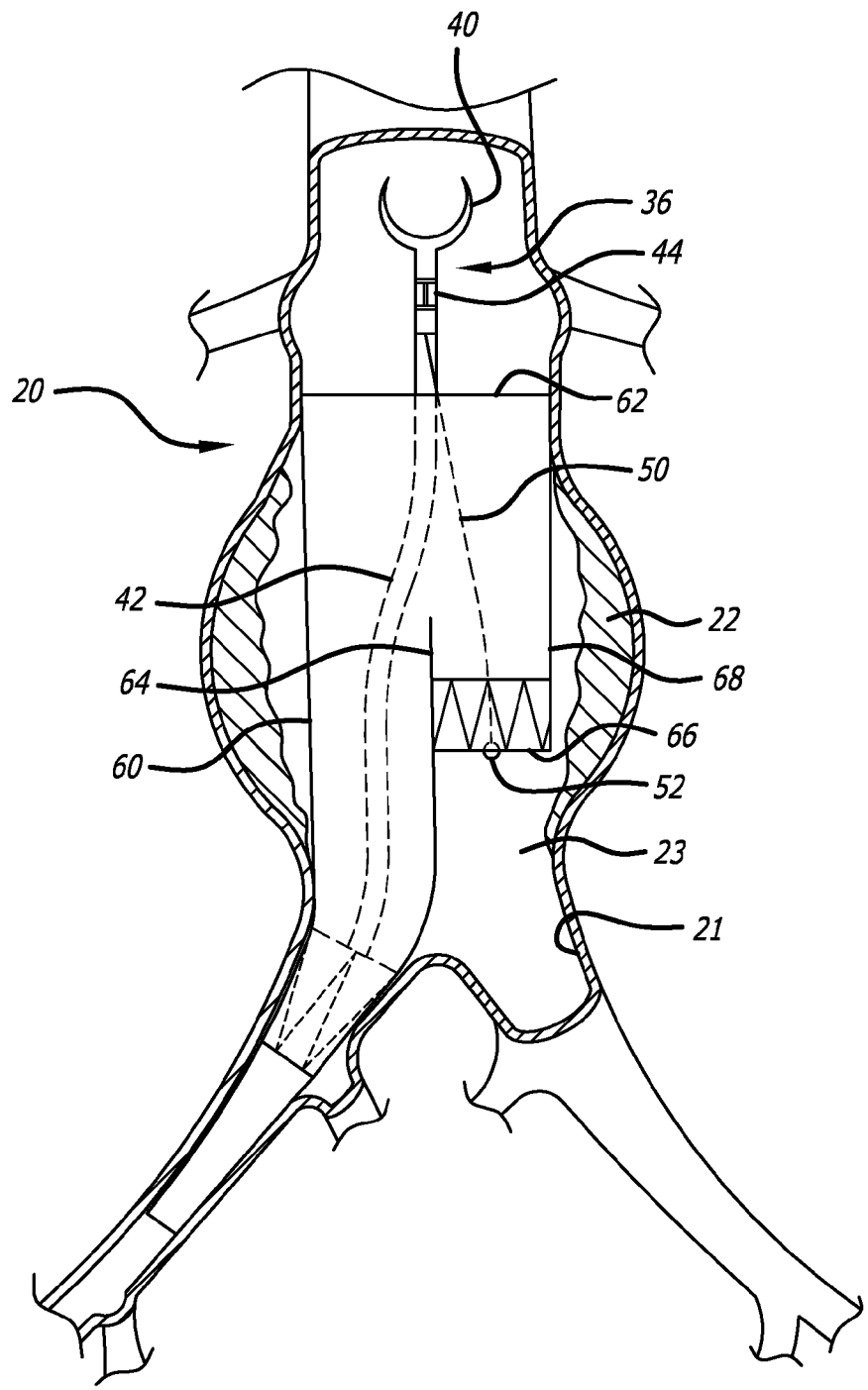
FIG. 3 is a partial cross-sectional side view, depicting the catheter of FIG. 2 inside a repair device deployed within vasculature.
Figure 4:
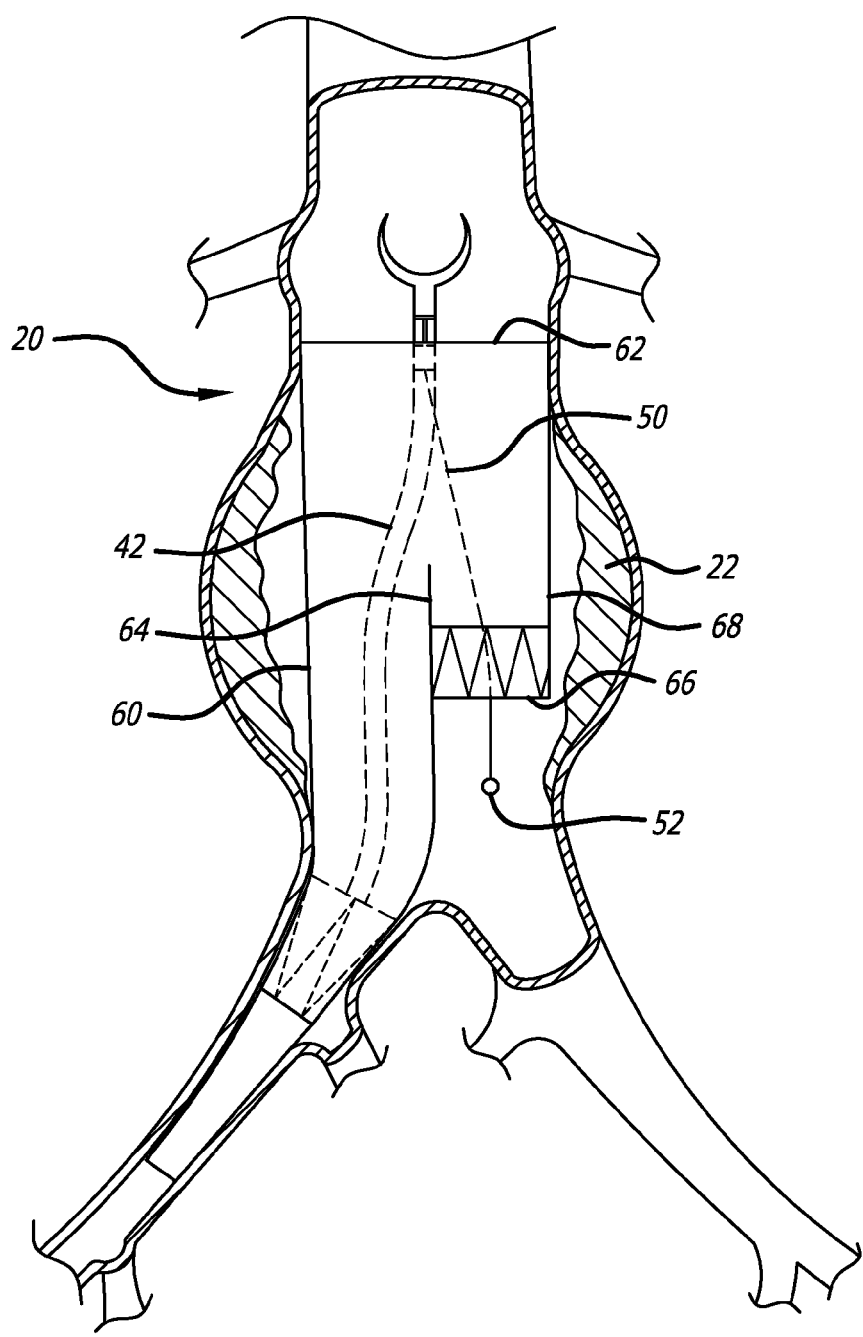
FIG. 4 is a partial cross-sectional view, depicting the assembly of FIG. 3 in which the snare target is positioned extending through a small opening in the repair device.
Figure 5:
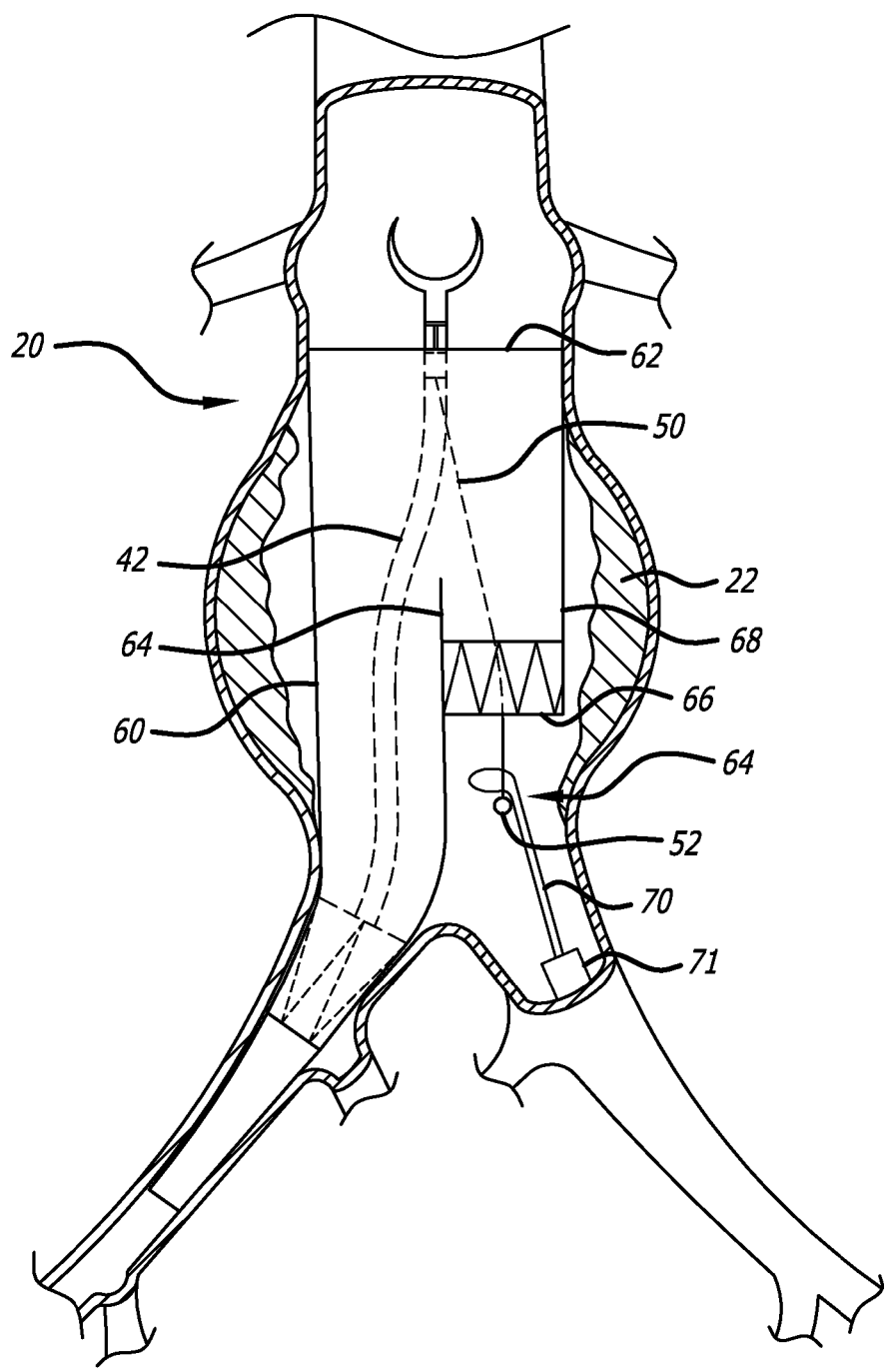
FIG. 5 is a partial cross-sectional view, depicting a snare placed into engagement with the snare target of FIG. 4.

The delivery system 30 further includes a snare target wire 50 having a terminal end configured with a snare target ball 52. The target wire can be made from a number of materials that allow the wire to be compressed to lay alongside of the main catheter shaft and then spring back to its laterally extending position as shown in FIGS. 2–4. One preferred material is nitinol. In another embodiment, the snare target wire can be retractable to within a lumen in the main catheter shaft for storage and extended to aid in the delivery procedure. In the embodiment shown, the snare target wire extends from the superior end of the main catheter 32 in an inferior direction. In an alternate embodiment it can be routed initially in a superior direction and then folded or bent to extend in an inferior direction. The target wire 50 is attached to the catheter 32 preferably by crimping a band over the wire and catheter but can be attached in other ways just as by adhesive or molding into the catheter.

Turning now to FIGS. 3–7, a method involving employing a system 30 including a snare target wire 50 is described. In a typical implant scenario, the delivery system 30 carrying a first endovascular component repair device 60 is advanced within vasculature to a repair site 22 and the jacket 38 is withdrawn to expose the superior portion of the main catheter 36. In the embodiment shown, the jacket is withdrawn far enough for contralateral opening 66 to open but still covering the ipsilateral portion of the repair device 60 so that the repair device is held relatively stable while contralateral opening 66 is cannulated. A superior end 62 of a repair device 60 is expanded or permitted to expand by withdrawing a release wire (not shown) to thereby be implanted in the region of the repair site. The target ball 52 of the target snare wire 50 is then positioned adjacent to a mating or engagement area 64. The mating or engagement area 64 in the scenario shown in the figures is adjacent and interior of a contralateral opening 66 of the repair device 60. The snare target wire 50 is pushed out through the contralateral opening 66 by moving the receiving portion 42 down while main catheter 32 is held relatively stable or by extending the wire 50 by a separate control (not shown) at the control handle of the delivery catheter so that the snare target ball 52 provides a target for engaging a snare 70.

In one contemplated method the system 30 is assembled so that the snare target ball 52 is initially positioned within a contralateral leg 68 of the repair device 60 so that withdrawal of the receiving portion 42 with respect to the repair device 60 causes the snare target ball 52 to exit the contralateral opening 66 of the repair device 60. Next, the snare 70 inside of its delivery catheter or sheath 71 can be advanced within vasculature to the engagement area 64 and the target wire with the target ball can be lowered into engagement with the snare loop. It is to be recognized that the delivery catheter or sheath 71 can be single or multi-lumened such as that described below so that an exchange need not be done. That is, for example, a second lumen can be incorporated into the delivery sheath and be configured for passage of an auxiliary guidewire that is contemplated to be used as a platform for other medical components or to maintain access to the repair site. Once the snare loop engages the snare target ball 52, the receiving portion 42 is moved in a superior direction to pull the snare 70 up within the repair device 60. Once the superior end of the snare catheter or sheath is within the opening 66 then the snare can be removed from within the snare catheter or sheath and a conventional guidewire passed up through the snare catheter or sheath into the repair device 60. The guidewire is left in place and the snare catheter or sheath is removed. Then a delivery catheter with the second modular repair device component is advanced over the guidewire. The second component is then released from the delivery catheter. The entire procedure can be observed using remote engaging techniques such as fluoroscopy. Where system 30 is used with other repair devices, such as one in which the ipsilateral portion of repair device 60 is long enough to reach into the iliac artery, similar relative motion can be used to position the snare target wire 50 at an engagement site and to accomplish joining component parts of a repair device or to simply gain access thereto. For example, the jacket would be withdrawn completely to allow opening 66 to open and the ipsilateral limb to anchor in the iliac artery. Then movement of the main catheter (as opposed to just the receiving portion 42) would position the snare target.

Figure 6:
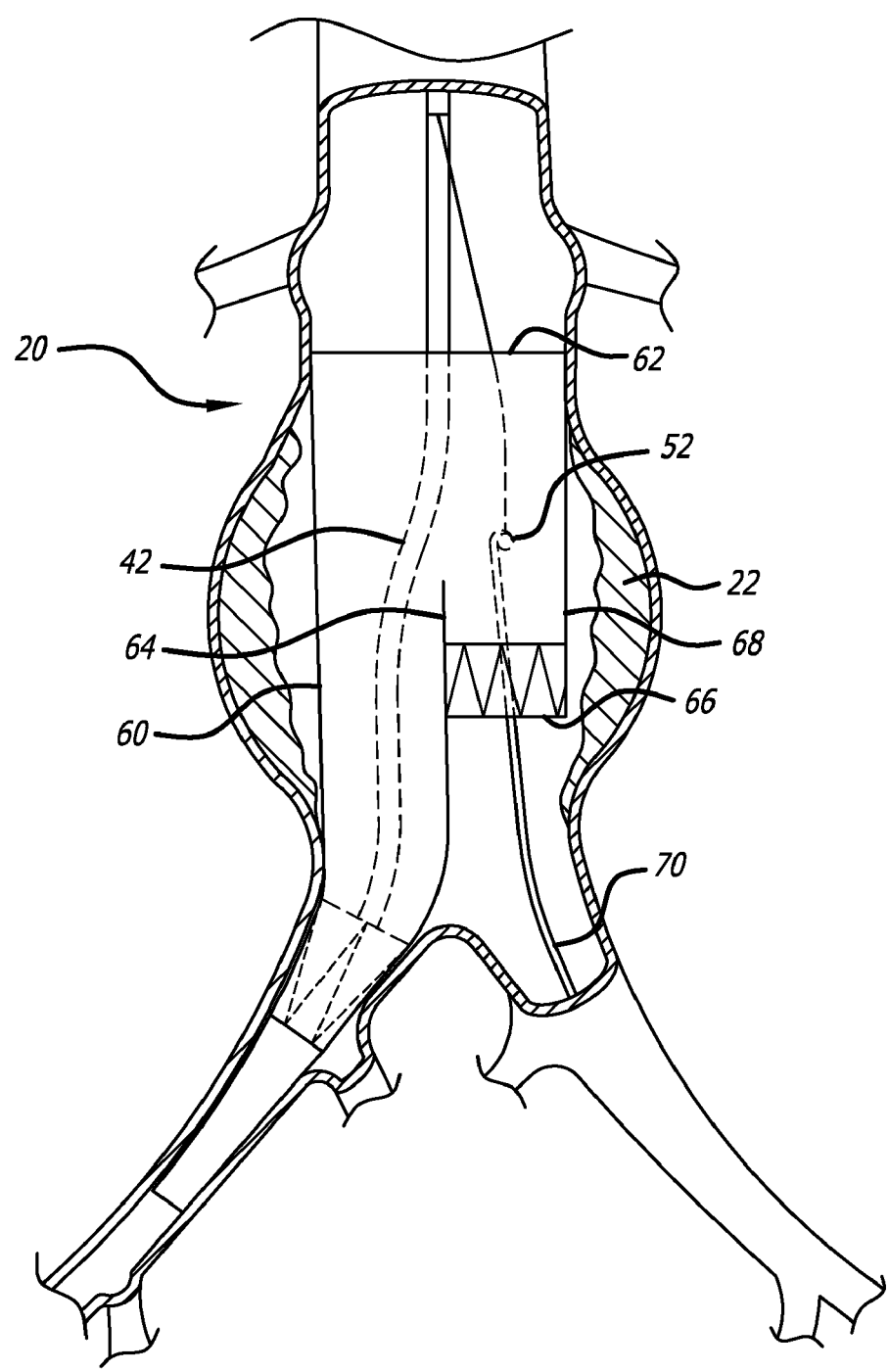
FIG. 6 is a partial cross-sectional view, depicting the superior advancement of the snare target and snare within the repair device.
Figure 7:
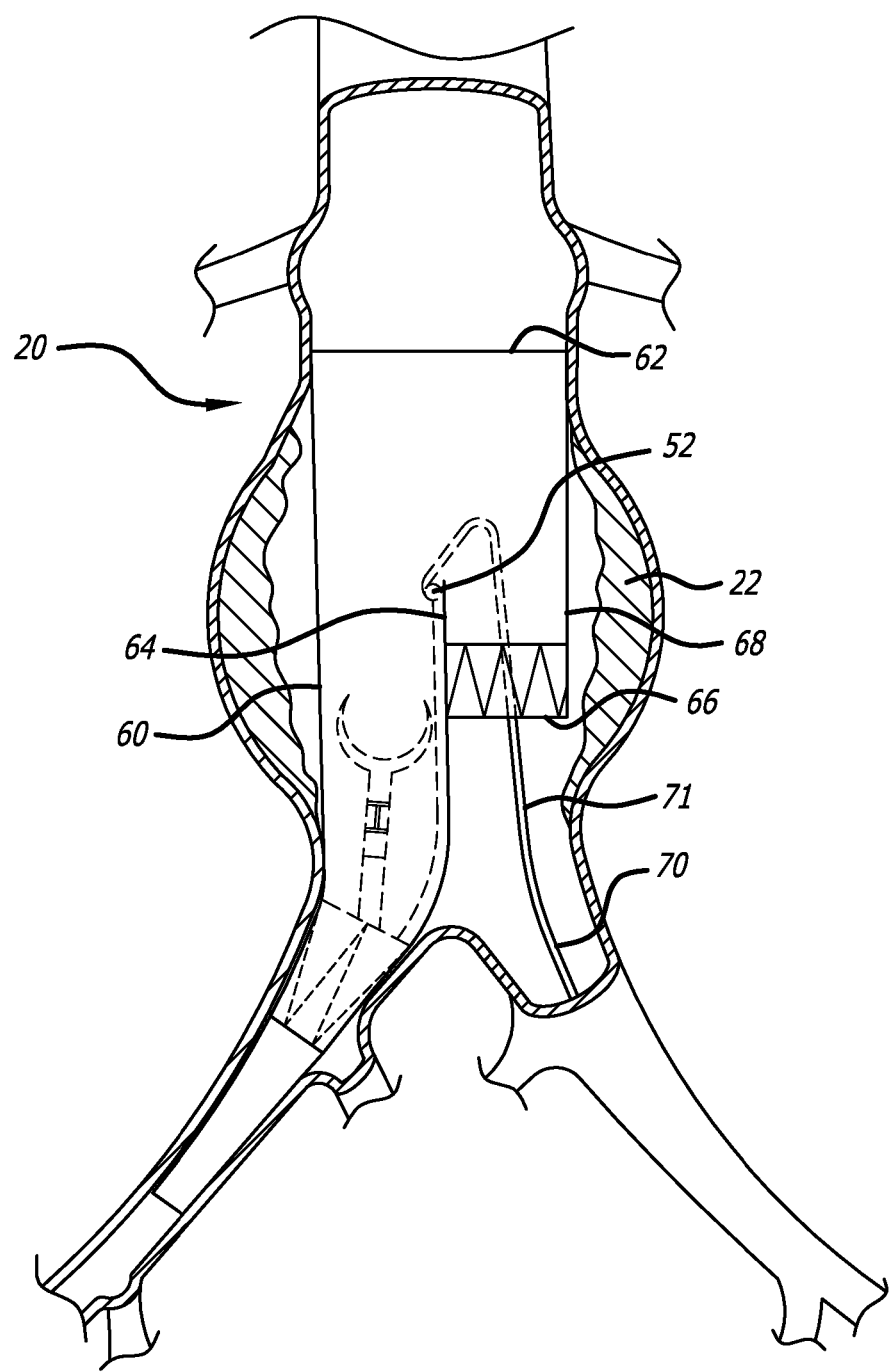
FIG. 7 is a partial cross-sectional view, depicting the retraction of the snare target and snare of FIG. 5 into the repair device.

If there is a desire to cross over the repair device bifurcation, the snare 70 can be pulled over a bifurcation 64 within the repair device 60 by moving the receiving portion 42 inferiorly as needed (see FIGS. 6 and 7).

To facilitate the engagement of the snare target ball 52 and the snare 70, it is contemplated that a soft magnet be used as a snare loop. The snare target ball 52 can have magnetic properties and is therefore contemplated to be made from ferromagnetic materials such as a ferritic stainless steel. The soft magnet can embody an Fe −44.4% Ni alloy or other equivalent materials with or without a thin protective coating provided for biocompatibility. In one aspect the snare embodies a loop so that in combination with a soft magnet, a closed-loop field is generated, one that does not interfere with other magnetic fields. Permanent magnets are less suitable for this application because they can potentially cause problems with other electrical equipment in an operating room and can also attract undesirable particles or small objects but they can be used.

Figure 8:
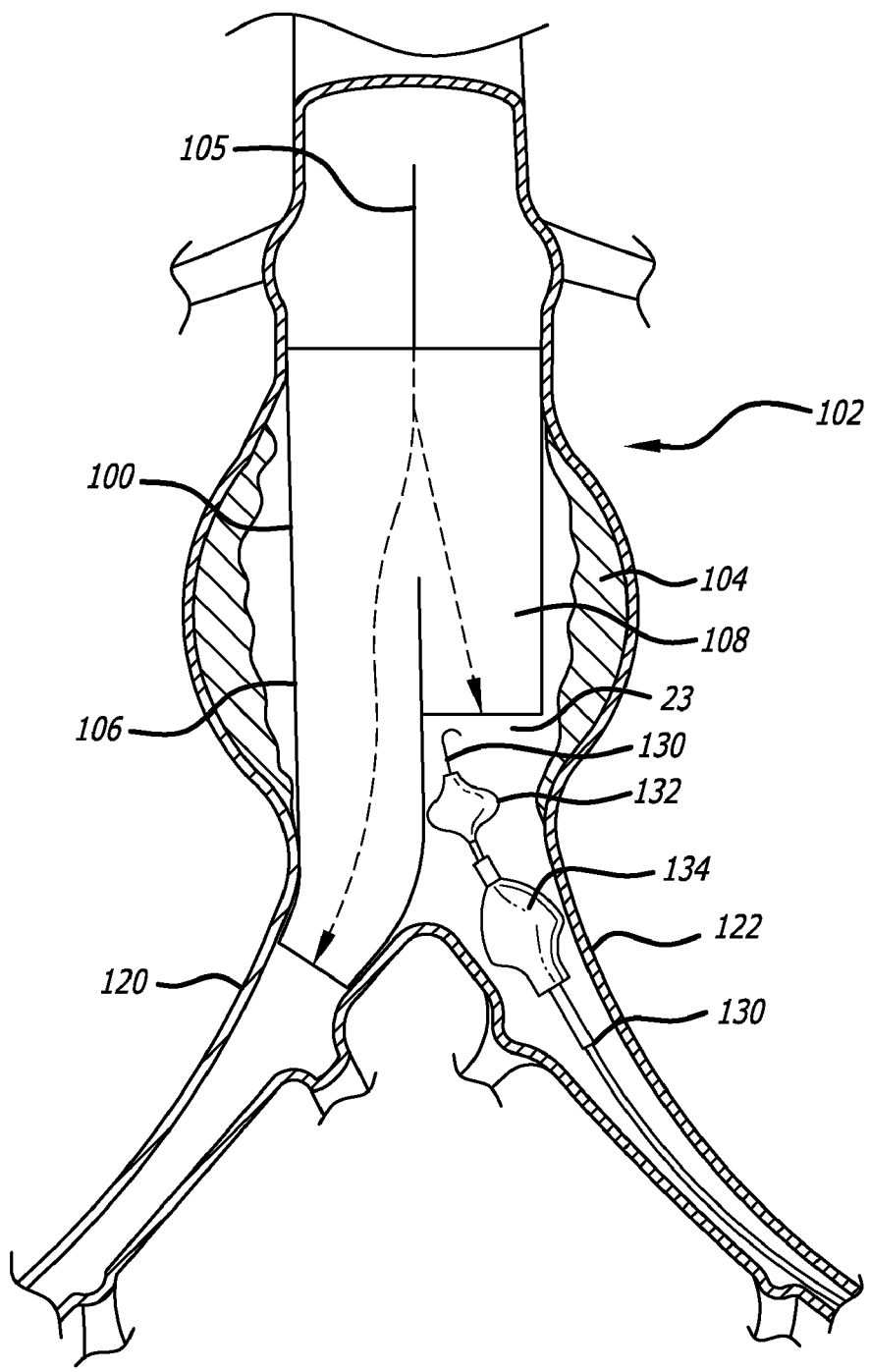
FIG. 8 is a partial cross-sectional view, depicting a first modular component of a repair device placed within vasculature and an expandable device placed to change the flow of blood.
Figure 9:
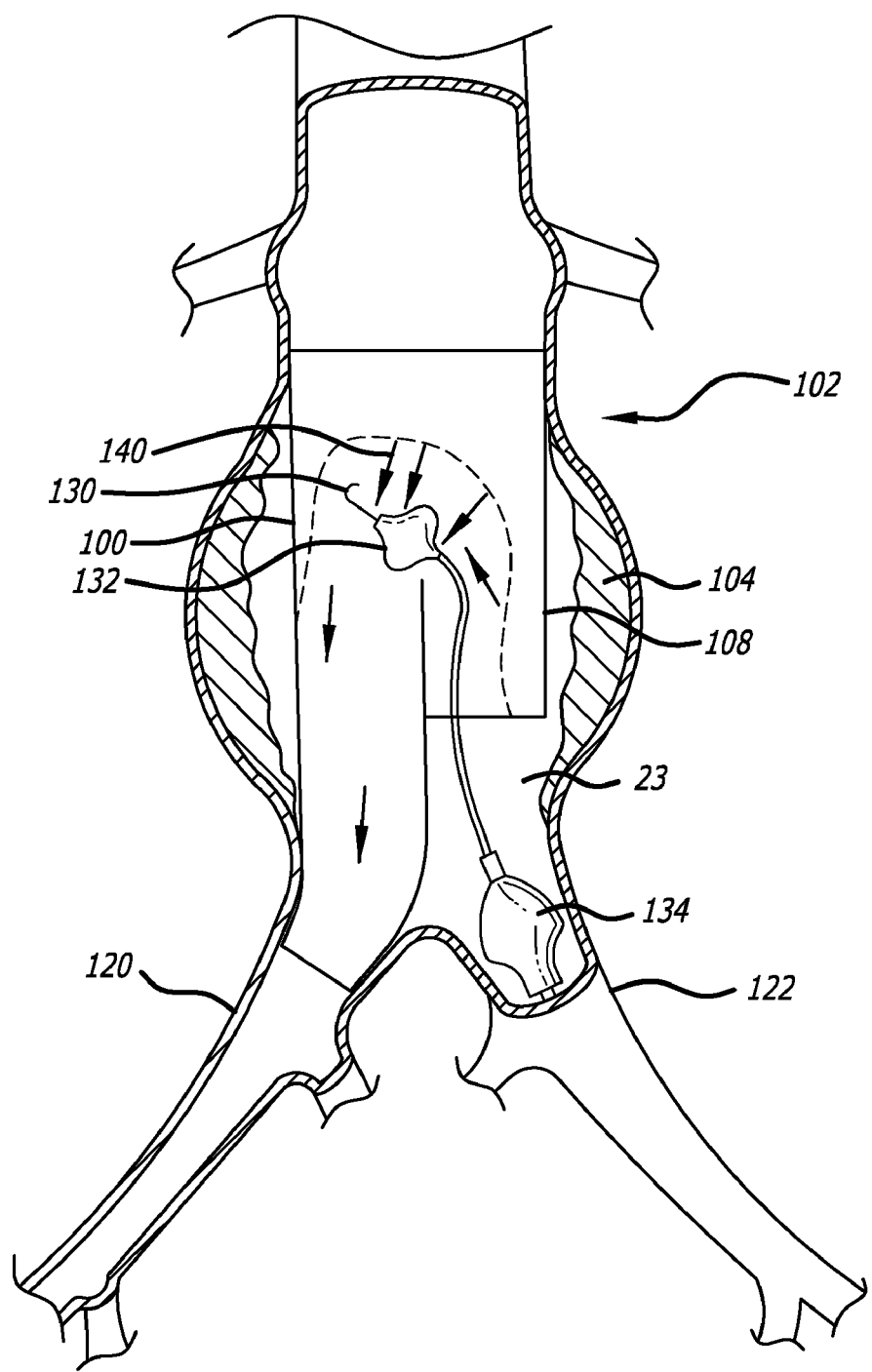
FIG. 9 is a partial cross-sectional view, depicting the expandable device of FIG. 8 advanced within a repair device with the aid of retrograde flow.

With reference to FIGS. 8 and 9, there is shown a portion of a modular repair device 100 which has been deployed within vasculature 102 at a repair site 104. In the implanted condition, blood is flowing in an inferior direction 105 through the repair device 100. In the embodiment depicted, the repair device 100 is in the form of a bifurcated graft with ipsilateral 106 and contralateral 108 limbs, the ipsilateral limb 106 being positioned in a first branch vessel 120. In order to attach an additional component to the contralateral limb 108 or to otherwise gain access to an interior of the repair device 100, a contralateral approach can be taken.

An elongate element in the form of a guidewire 130 is placed within vasculature and advanced through a second branch vessel 122 to the vicinity of the repair site 104. A superior end of the guidewire 130 is equipped with an expandable member 132 and an expandable occlusive member 134 designed to cause a pressure gradient within the vasculature sufficient to create retrograde flow within cavity space 23 and limb 108. Occlusive member 134 and the expandable member 132 can be in the form of inflatable balloons and the guidewire is formed from a hypotube. The balloons can be configured with multi-lumen cores or concentric lumens that allow a guidewire to pass through.

In a method of use, while positioned adjacent to the repair site, the expandable occlusion member 134 is expanded to block flow through the second branch vessel 122. Being that the flow of blood has only one major outlet, namely through the first branch vessel via the repair device 100, the vasculature is primed for retrograde flow within cavity space 23 and limb 108. Once the "floppy" expandable member 132 is advanced it is permitted to follow the path 140 (FIG. 9) taken by the retrograde flow through the repair device 100. In this way, the guidewire 130 can be selectively placed within the repair device 100. Such a method can be employed to advance any member to or within a target site within vasculature.

Figure 10:
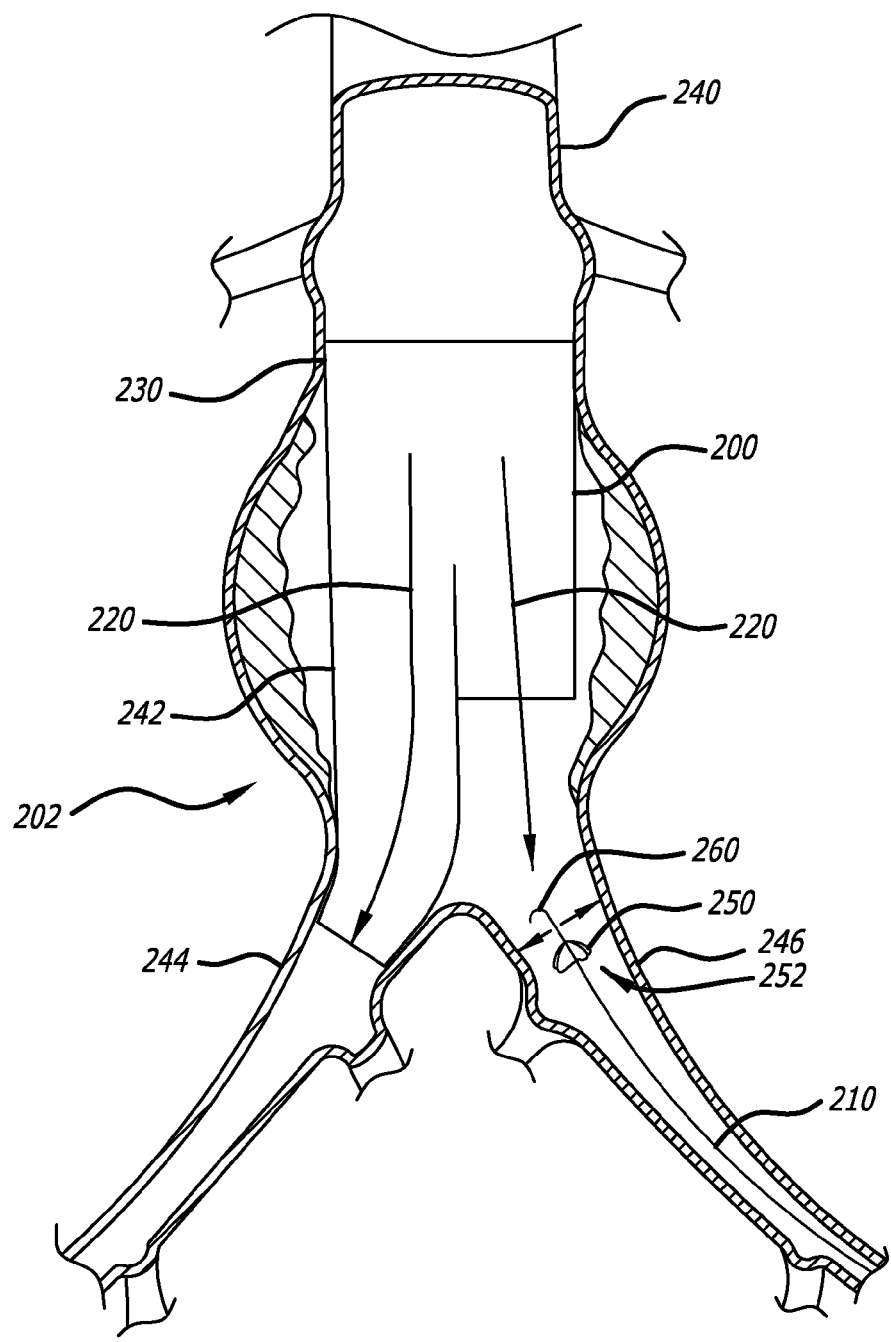
FIG. 10 is a partial cross-sectional view, depicting a system placed in vasculature that is responsive to blood flow.
Figure 11:
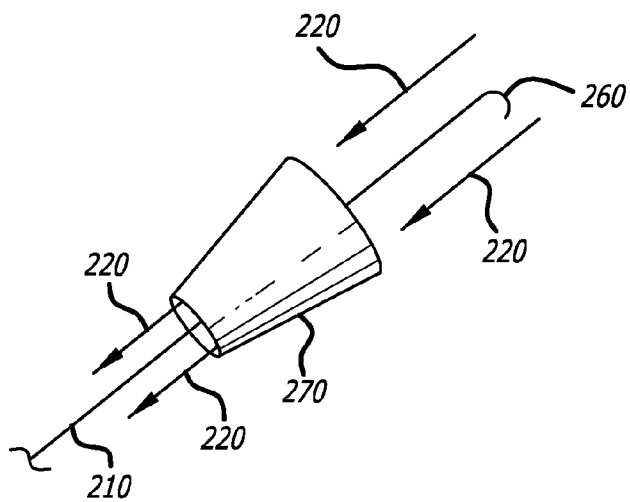
FIG. 11 is a side view, depicting an alternative embodiment of a device responsive to blood flow.

In another aspect of the invention, flow of blood in the inferior direction is utilized to aid in directing a medical component in a superior direction to a target. As shown in FIGS. 10 and 11, with a repair device 200 in place in a bifurcated section of vasculature 202, a medical device 210 can be advanced against flow 220 of blood to a target site. In the depicted embodiment, a superior end 230 of a repair device 200 in the form of a bifurcated graft component is implanted at a superior location of a main vessel 240. An ipsilateral leg portion 242 of the graft is implanted in a first branch vessel 244. Flow of blood is traveling through the graft 200 from the main vessel 240 to the first 244 and second 246 branch vessels. An elongate guidewire or other medical device configured with rudders or fins 250 at a superior end portion 252 is advanced through the second branch vessel 246 proximate to the repair site where the graft 200 has been implanted.

Due to the rudders or fins 250, the guidewire 210 is provided with physical and visual feedback regarding its advancement to within or to an engagement junction with the graft or repair device. Like a jet fighter landing on an aircraft carrier using laser guided feedback, any misdirection through the flow 220 results in pushing a tip 260 of the guidewire 210 away in a dramatic fashion, thus providing important physical and visual feedback (under remote imaging) to the goal of guidewires or other medical devices reaching a target. Moreover, by embodying a plurality of rudders or fins 250, the medical device can be enabled to progress straight through the inferior flow to the desired destination.

As shown in FIG. 11, the guidewire 210 could alternatively be configured with other structure capable of taking advantage of inferior flow such as an open sock structure 270. The open sock acts to funnel and steer the guidewire to a mating junction by allowing flow 220 in and out, in line with the guidewire tip 260. In order to enhance the effect of flow through which it is desirable to advance a medical device, steps can be taken to close one or more branch vessels in the vicinity. For example, a balloon catheter (not shown) can be employed to cease flow in a branch vessel 244 so that the majority of blood flowing in the areas passes through the second branch vessel 246.

Figure 12:
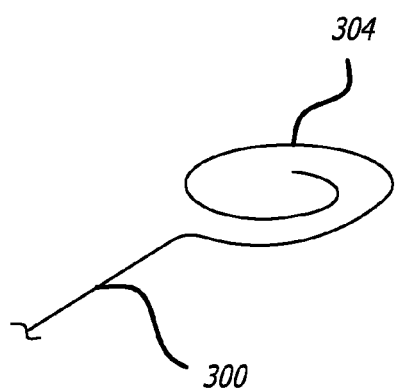
FIG. 12 is a side view, depicting one embodiment of a curved terminal end of an elongate member.
Figure 13:
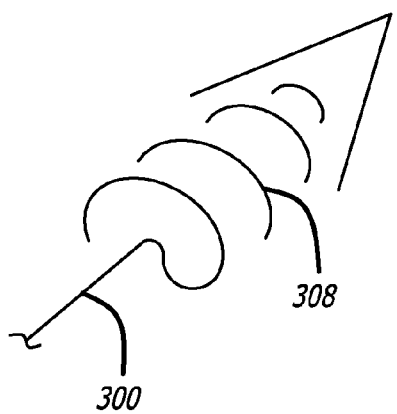
FIG. 13 is a side view, depicting a second embodiment of a curved terminal end of an elongate member.
Figure 14:
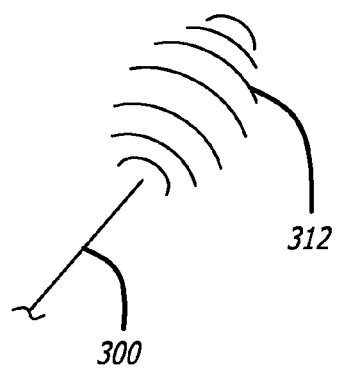
FIG. 14 is a side view, depicting a third embodiment of a curved terminal end of an elongate member.

Turning now to FIGS. 12–14, there is shown medical devices with various configurations of terminal ends. Each of the depicted medical devices include enlarged terminal ends providing an increased surface area for engaging or accessing a target. For example, an elongate guidewire or other medical device 300 can be configured with a flat spiral structure 304 (FIG. 12), a conical structure 308 (FIG. 13) or a spherical structure 312 (FIG. 14). Such structures can be formed by coiling the elongate member or by other equivalent methods. In all cases, it is contemplated that the enlarged terminal ends be reduced in cross-section as needed.

In one aspect, the terminal ends are contemplated to be placed in a substantially straightened configuration by manipulating an inferior end portion of the particular medical device 300. In this way, the medical device 300 can assume an enlarged profile for aid in reaching the target site and then take on a small profile for insertion into the target or for the purpose of simply taking up less room. The devices can therefore be employed to engage or gain access to an opening in a graft or other repair device, for example, so that a path can be made for assembling components embodying the graft or repair device in situ as previously described.

Figure 15:
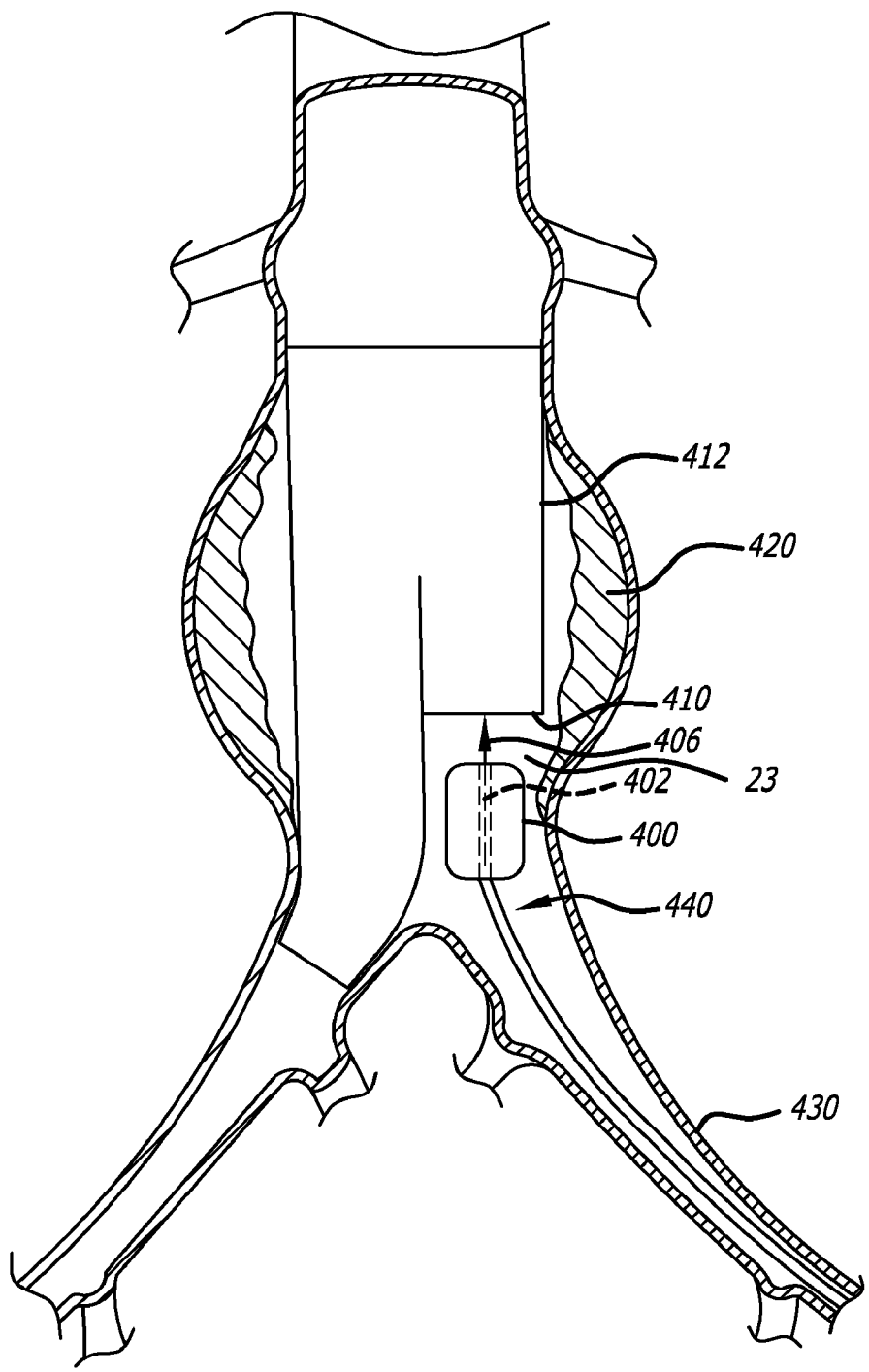
FIG. 15 is a partial cross-sectional view, depicting a device for creating a temporary pathway within vasculature.

Another approach to accomplishing the in situ assembly of a repair device is shown in FIG. 15. This embodiment reduces or eliminates lateral movement of a guidewire within vasculature to thereby provide a more direct path across cavity space 23 to a target. As with the use of retrograde and inferior flows, providing a more direct path by reducing lateral movement helps to compensate for difficulties associated with attempting three-dimensional procedures while observing the procedure via two-dimensional fluoroscopic techniques. These approaches also facilitate accomplishing the difficult task of hitting remote targets with free floating ends of elongate members. In one aspect of the present approach, an expandable member, for example, a balloon 400 configured with an interior pathway 402 is placed inferior a target site in cavity space 23 or partially inside vessel 430. In the scenario depicted in the figures, the balloon 400 is providing a pathway 406 to a contralateral opening 410 in a repair device 412 that has been partially implanted at a repair site 420.

Various devices can be provided to accomplish placement of an expandable member 400 adjacent to a target within vasculature. A system like that shown in FIG. 2 could be employed except the snare target wire 50 could be replaced with a tubular structure having a terminal end configured with a balloon 400. In such an arrangement, the tubular structure would be placed in fluid communication with a conventional pump or syringe to achieve expansion of the balloon 400. Alternatively, the balloon 400 could be a terminal end of a catheter 440 placed within the branch vessel 430 in line with the contralateral opening 410 or ultimate target. In yet other aspects, the expandable member can embody a permanent or temporary tampon structure such as collagen that is strategically placed to provide a path to the destination envisioned for an elongate guidewire or medical device.

Other methods and devices are contemplated to solve problems associated with in situ assembly. Several methods rely upon a second catheter placed in a second branch vessel to provide a stabilizing location upon which a first catheter placed in a first branch vessel may be temporarily secured while maneuvering a guidewire from the first catheter to a desired destination.

Figure 16:
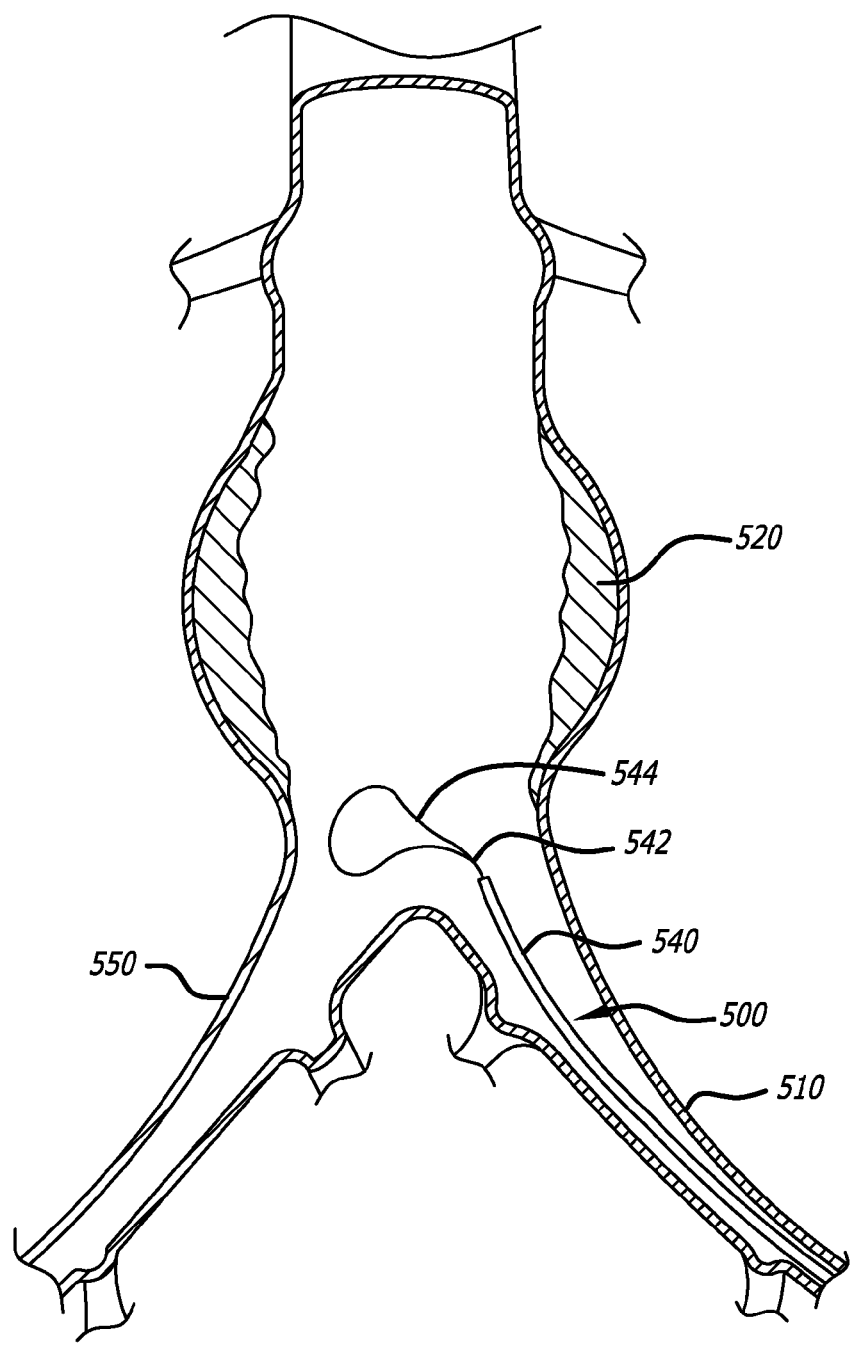
FIG. 16 is a partial cross-sectional view, depicting a snare device deployed within vasculature.
Figure 17:
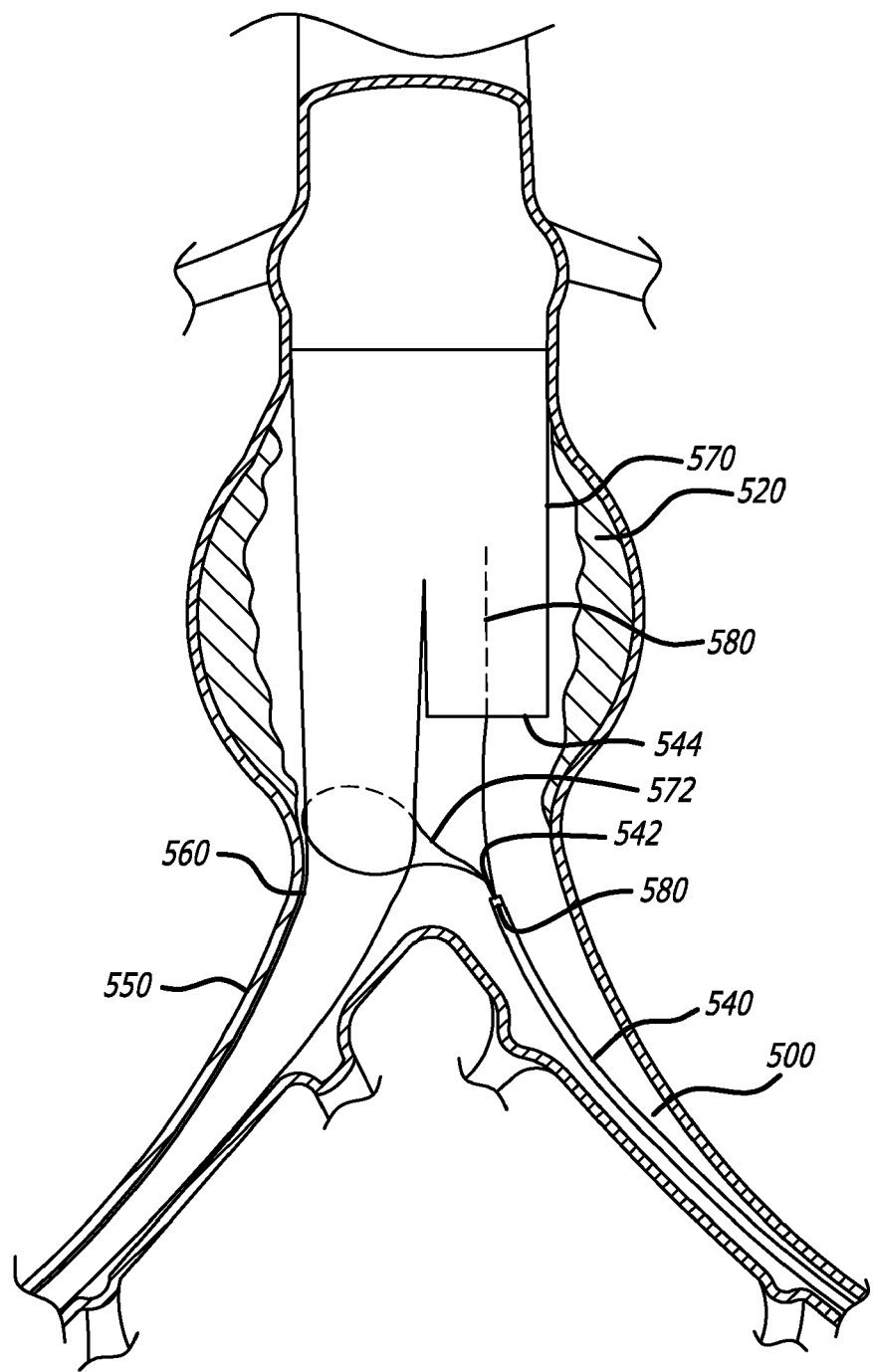
FIG. 17 is a partial cross-sectional view, depicting an in-situ assembly method involving the snare of FIG. 16.

As shown in FIGS. 16 and 17, a snare catheter 500 can be placed within vasculature and configured to extend from a first branch vessel 510 to a main vessel 520. The snare catheter 500 embodies an elongate tubular member 540 having an internal lumen that slideably receives an elongate member or snare 542 having a terminal end defining a loop or other capture structure 544. Upon relative movement between the elongate member or snare 542 and the elongate tubular member 540, the capture structure 544 is placed in a position to engage or receive a delivery catheter 560 carrying a repair device 570, such as a bifurcated graft, that is placed to extend from a second branch vessel 550 to within the main vessel 520.

In order to accomplish in situ assembly of repair device components or to gain access to a target, the snare catheter 540 further includes a marker (not shown) that aids in orienting the snare catheter 540 with the target. In FIG. 17, the target is shown as an opening 572 in a limb of a bifurcated graft 570. The terminal end of the snare catheter 540 can be equipped with a marker 580 that is aligned with a marker associated with the opening 572 or other structure placed at the repair site. Once marker alignment is achieved, a guidewire 590 is advanced through the snare catheter 540 to the desired destination. In one contemplated aspect, the guidewire 590 is advanced through a second lumen formed in the snare catheter or is provided by way of tearaway structure of the snare catheter.

Figure 18:
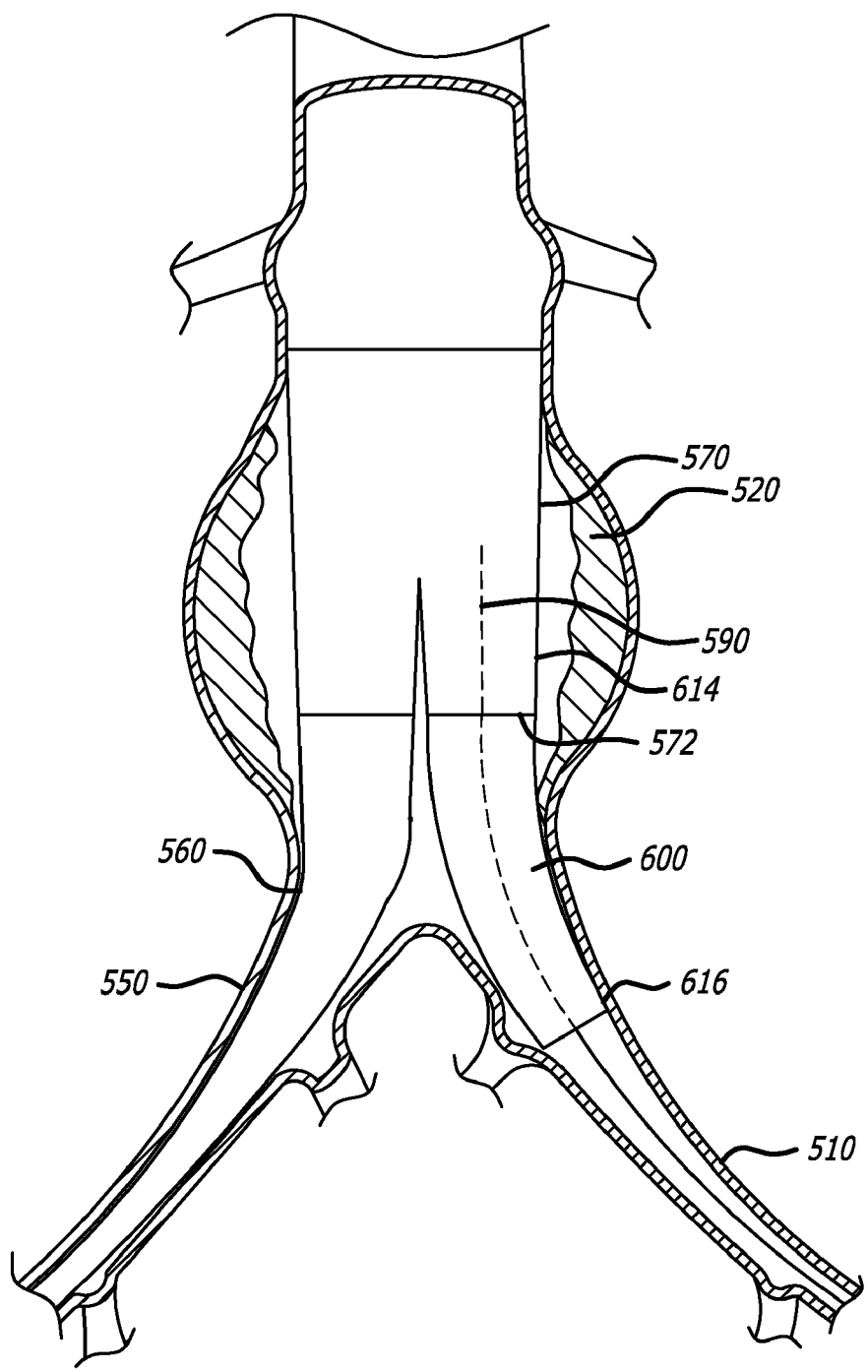
FIG. 18 is a partial cross-sectional view, depicting a limb component attached to a main body component utilizing a method involving the snare of FIG. 16.

Upon placement of the guidewire at the appropriate destination, further components can be delivered to the repair site or further procedures can be performed using the guidewire as a platform. For example, as shown in FIG. 18, a limb component 600 may be delivered and deployed inside the opening 572, with the superior end 614 of the limb component attached to the limb of the bifurcated graft 570 and the inferior end 616 anchored in the vessel 510. To help guide the elongate tubular member 540 and the capture structure 544 one or more asymmetric or concentrically arranged balloon members can be incorporated into the snare catheter 500.

A crimped tubular leg graft, generally designated 600, is shown in FIGS. 19 and 20, and may be used in connection with the bifurcated graft 570 shown in FIGS. 16–18. The crimped tubular legs 600 of FIGS. 19 and 20 each have a tubular body 612 with superior 614 and inferior 616 ends. There is a superior cylinder 618 located at the superior end 614 of the tubular leg 600 with a specific diameter including a lock stent 620 having hooks 621 to secure the tubular leg to the main limb implant, for example, at the opening 572 in bifurcated graft 570. The tubular leg 600 also includes a crimped cylinder 622 with a plurality of crimps 624 along a longitudinal axis, and an uncrimped flared cylinder 626. At the inferior end 616 of the tubular leg 600 is an inferior cylinder 628 with a specific diameter including a limb stent 630 and hooks 634 for securing the tubular leg to the corporeal lumen, for example, first branch vessel 510. The diameter of the inferior cylinder 628 can vary in size depending on the size of the vessel where it will be located.

Referring to FIG. 19, a tubular leg 600 is shown where the diameter of the inferior cylinder 628 is larger than the diameter of the superior cylinder 618. The tubular leg 600 in FIG. 19 has a pattern from the superior end 614 to the inferior end 616, starting with the superior cylinder 618 with the lock stent 620, followed by the crimped cylinder 622, which leads to the uncrimped flared cylinder 626 that flares out to the larger diameter of the inferior cylinder 628 with the limb stent 630. The diameter of the crimped cylinder 622 is essentially equal to the diameter of the superior cylinder 618.

Referring now to FIG. 20, the tubular leg 600 has an inferior cylinder 628 with a diameter smaller than the diameter of the superior cylinder 614. The tubular leg 600 in FIG. 20 has a pattern from the superior end 614 to the inferior end 616, starting with the superior cylinder 618 with the lock stent 620, followed by the uncrimped flared cylinder 626 that flares out toward the superior end and tapers down to the smaller diameter of the crimped cylinder 622 which follows, and leads into the inferior cylinder 628 with the limb stent 630. The diameter of the crimped cylinder 622 is essentially equal to the diameter of the inferior cylinder 628.

The lock stent 620 shown in FIGS. 19 and 20 is located internal to the graft material and is self-expanding with a series of caudal hooks or barbs 621 that extend through relief holes 632 that are spaced around the circumference of the superior cylinder 618 to correspond to the hooks or barbs 621. The lock stent 620 is attached to the superior cylinder 618 using sutures such that the hooks or barbs 621 protrude through the holes 632 when the tubular leg 600 is compressed for delivery, thereby preventing the compressed hook or barb 621 from tearing the graft material. The lock stent 620 is designed to be attached to an inferior end of the bifurcated graft 570 inside either the ipsilateral or contralateral leg. It is preferred that there are five hooks or barbs 621 equally spaced around the lock stent 620, however the number of hooks can vary.

The limb stent 630 is also self-expanding and is designed to be attached to the vessel wall to anchor the inferior end 616 of the tubular leg 600. The limb stent 630 can be located internal to the graft material of the inferior cylinder 628 as shown in FIG. 19, or it may be located on the exterior of the inferior cylinder as shown in FIG. 20, however it is preferred for the limb stent to be on the interior (internal to graft material) to aid in the apposition of graft material to the wall of the vessel for purposes of sealing the anastomosis. The limb stent 630 is shown to have three hooks 634 extending beyond the inferior end 616 of the tubular leg, however any number of hooks may be used, and they may also be located inside the inferior cylinder 628 and extending through relief holes.

Note that the hooks or barbs 621 at the superior end 614 are angled in the inferior direction, which is the direction of blood flow in the vessel. This angling helps to ensure better attachment of the tubular leg 600 to the main implant 570. The barbs on the inferior end 616 of the tubular leg point opposite to the blood flow. When the tubular leg 600 is compressed for delivery, the hooks or barbs 621 and 634 of the stents 620 and 630 are also at least partially compressed. In a preferred embodiment, the relief holes 632 are pre-punctured using a hot pin to melt the graft material, or ultrasonically punched, allowing the five stent hooks 621 to protrude through the graft material when the tubular leg 600 is compressed for delivery. When the tubular leg 600 is deployed within the ipsilateral or contralateral limb of a main implant 570, the stent 620 will expand, thereby causing the hooks 621 to penetrate the graft material of the main body component 570, forming a seal and anchoring the tubular leg 600 within the main body component 570. A balloon can also be used to set the hooks. A "tug" in the distal direction can also set the hooks.

Radiopaque markers 633 are also disposed on the surfaces of the tubular legs 600 as shown in FIGS. 19 and 20. In this embodiment, a pair of markers 633 are aligned longitudinally along the tubular leg 600 and are attached to the crimped cylinder and the uncrimped flared cylinder. The alignment of two markers 633 along the tubular graft is enough to show twists when the graft is viewed under fluoroscopy. An asymmetric pattern of markers 633 may also be disposed along the tubular graft 600. The embodiments shown in the figures also include radiopaque markers 633 attached to the superior end 614 of the leg 600 and the inferior end 616 of the leg to indicate under fluoroscopy where the ends of the tubular leg are located inside the vessel. The pair of markers 633 aligned on the tubular leg 600 are spaced two crimps from each other, and about 7 mm–9 mm from the inferior edge of the lock stent 620 to the first pair of radiopaque markers. The pair of markers 633 disposed on the uncrimped flared cylinder 626 nearest to the crimped cylinder 622 are spaced about 11 mm–13 mm from the nearest pair of markers located on the crimped cylinder. Although the figures show nine pairs of markers 633 aligned on the tubular leg 600, the number may vary depending on the length of the tubular graft. The size of the markers 633 may vary and the location of the pairs of markers may also vary on the tubular legs 600.

The above embodiments are used by visualizing the marker images under fluoroscopy during deployment of the implant. An operator can observe the relative position and/or movement of the marker images during the procedure to help ensure proper deployment of the implant. The marker patterns can also be viewed post procedure on a still image to see the orientation of the implant in the vessel.

Figure 21:
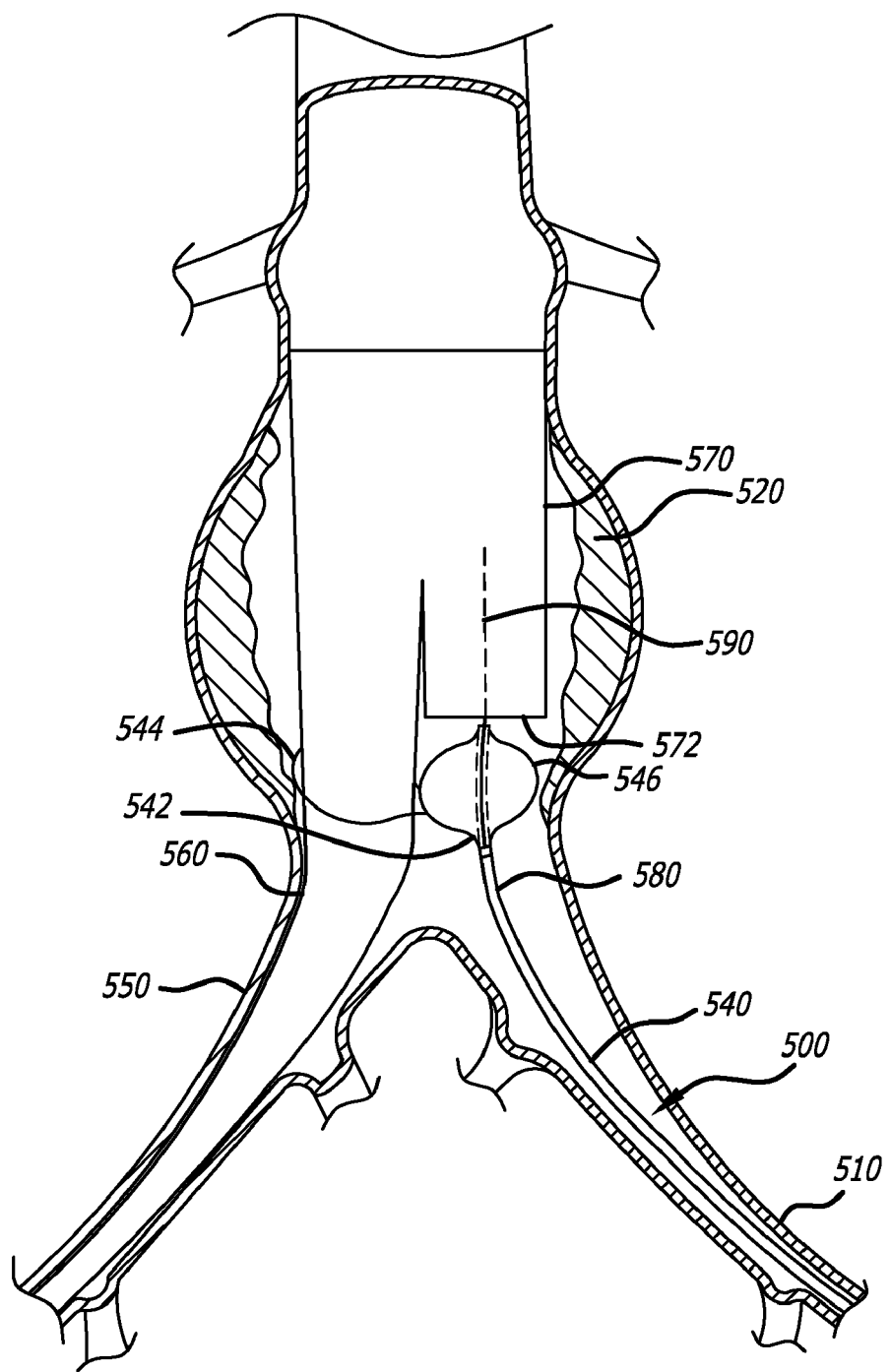
FIG. 21 is a side elevational view, depicting another embodiment of the snare of FIG. 16.

As shown in FIG. 21, the snare catheter 500 may also include an expandable member 546 to aid in the precise positioning of the guidewire 590 at the desired destination. With the capture structure 544 engaging the delivery catheter 560, the guidewire 590 may be adjacent the delivery catheter rather than directly under the desired destination, for example the opening 572 in the contralateral port of a bifurcated graft 570. The expandable member 546, for example a balloon or equivalent means, facilitates displacing or deflecting the tip of the guidewire 590 a given distance away from the adjacent delivery catheter 560 so that it is precisely under the opening 572.

With the tip of the guidewire 590 positioned along the radial path of the center of the opening 572, advancing the guidewire would likely facilitate rapid cannulation of the contralateral port. Even if the tip of the guidewire 590 is not precisely positioned along the radial path of the center of the opening 572, it is likely to be along the radial/orbiting path of the center of the opening such that torquable manipulation of the snare catheter 500 to rotate around and relative to the radial path of the center of the opening would precisely position the tip of the guidewire and facilitate rapid cannulation.

Since the contralateral port of the bifurcated graft 570 is a relatively constant distance from the delivery catheter 560 placed in the ipsilateral branch vessel 550, the expandable member 546 may be designed to displace the tip of the guidewire 590 that distance. It is further contemplated that the expandable member 546 may be slowly expanded and the marker 580 utilized to monitor the guidewire 590 tip in order to precisely position the tip relative to the marker associated with the opening 572. In one embodiment, the expandable member 546 is positioned adjacent the snare catheter 500 such that inflation of the expandable member does not force the tip of the guidewire 590 away from the opening 572 and expansion of the member displaces only the guidewire tip.

When the delivery catheter 560 is placed in the second branch or ipsilateral vessel 550 such that it extends into the main vessel 520 and the repair device 570 is partially deployed, the target, for example the opening 572 in the contralateral port, may still be a moderate distance from the delivery catheter. Cannulation of the contralateral port, a three-dimensional process, must be accomplished while viewed through a two-dimensional fluoroscope and, therefore, may not be accomplished in a timely manner.

Figure 22:
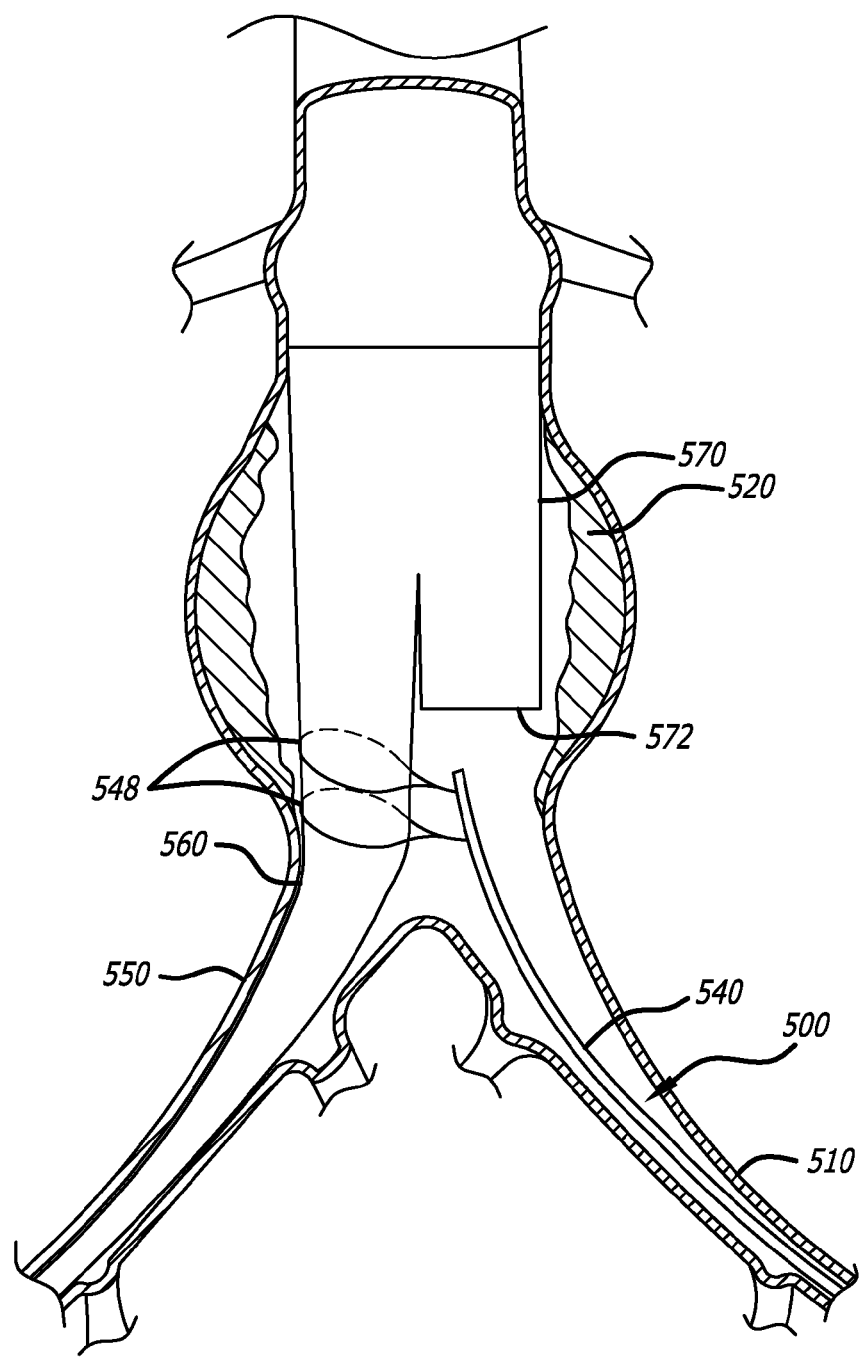
FIG. 22 is a side elevational view, depicting another embodiment of the snare of FIG. 16.
Figure 23:
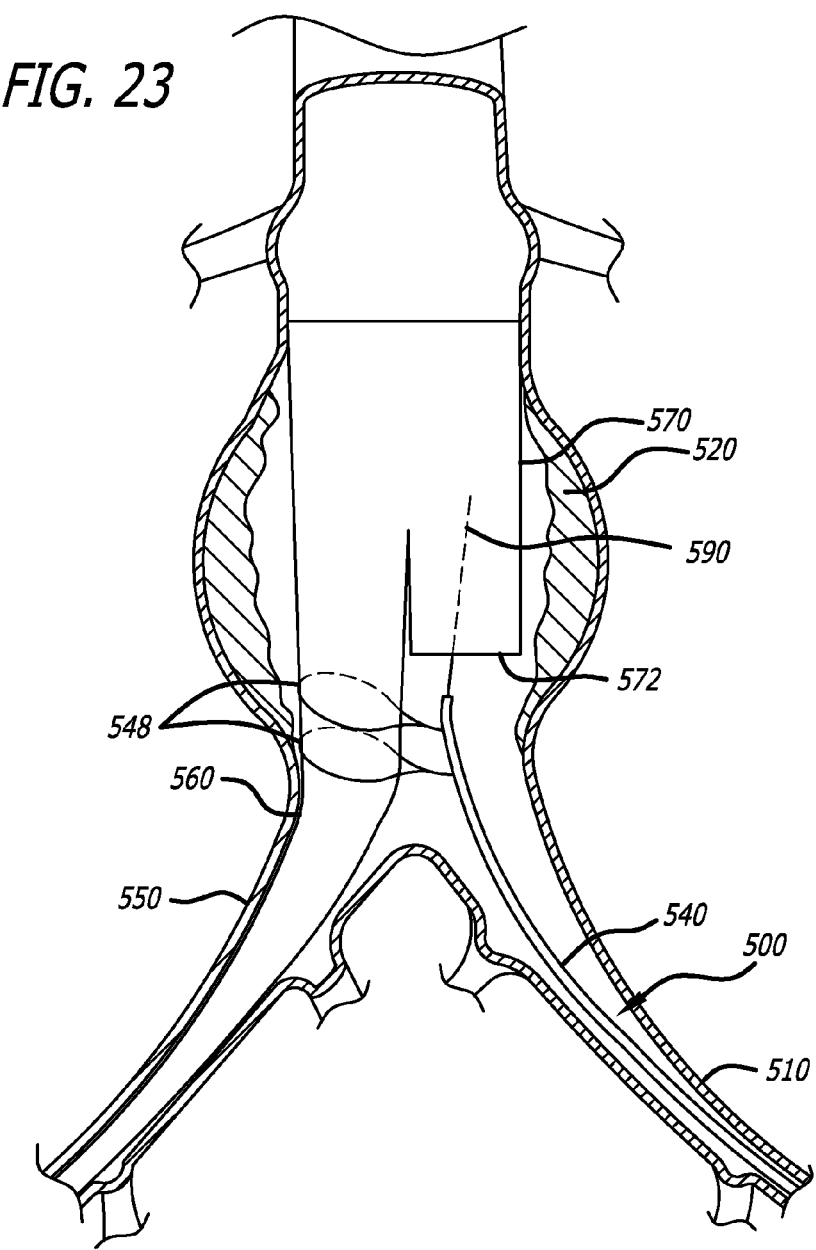
FIG. 23 is a side elevational view, depicting an in-situ assembly method involving the snare of FIG. 22.

As shown in FIGS. 22 and 23, the snare catheter 500 may include fins 548 rather than the elongate snare 542. In one aspect, the fins 548 can be defined by loops or similar structures deployed under a thin compliant webbing or skin such as a web foot. In another aspect, the fins 548 can be defined by partial hooked members that are heat set so that terminal ends of the hooked members return to a slightly spaced configuration for grabbing. In this way, the delivery catheter 560 need not pass through both fins 548 at any given stage. Additionally, the fins 548 may be used to align the snare catheter 500 adjacent to the delivery catheter 560 in a fixed plane, thereby providing tactile constraints that reduce the alignment and orientation of the guidewire 590 tip from a three-dimensional process to a two-dimensional process. Manipulation of the guidewire 590 tip is much easier as a two-dimensional process and cannulation of the contralateral port is simplified.

In one method of use, one of the fins 548 is actuated such that it projects from the snare catheter 500 and the snare catheter is rotated until physical contact is made with the delivery catheter 560. At this point, rotation of the snare catheter 500 is partially restrained. A second fin 548 is then actuated, the second fin designed to constrain or "saddle" the delivery catheter 560 between the two fins. Further actuation or manipulation of the fins 548 may bring them closer together or further apart, thereby translating the snare catheter 500 further from or closer to the delivery catheter 560 and, by moderate or incremental rotation about the delivery catheter, the tip of the guidewire 590 may be precisely oriented with the opening 572. The snare catheter 500 may also be advanced in the superior or inferior directions in order to bring the guidewire tip 590 closer to or further from the opening 572. Upon withdrawal of the delivery catheter 560, the snare catheter 500 can be retracted and removed from the repair site.

Figure 24:
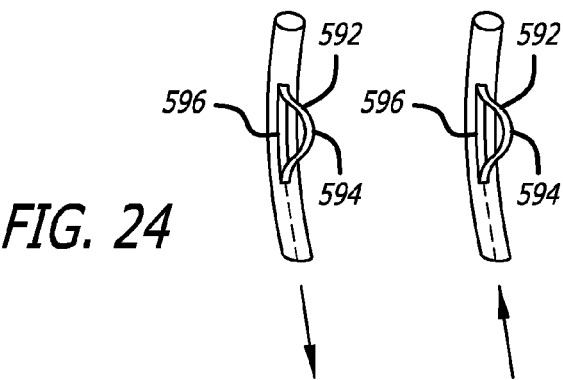
FIG. 24 is a partial perspective view, depicting the superior end of the snare of FIG. 22.

In one embodiment shown in FIG. 24, a multi-lumen snare catheter 500 with an 0.035" guidewire lumen may be used to pass parallel superelastic wires 592, 594 to be exposed through a long skive 596 and fixed at the superior end, causing the exposed wires to buckle out of the skive and project as two-dimensional fins 548. The diameter or heat-set shape of the wires 592, 594 may vary such that modulating the amount of buckling (i.e. by retracting or extending the wires in the direction of the arrows in FIG. 24) may alter how close the fins 548 allow the snare catheter 500 to come in proximity to the delivery catheter 560. It is contemplated that the wires 592, 594 may be covered or uncovered. It is further contemplated that the wires 592, 594 may be more mechanically actuated to project from the snare catheter 500 or more visceral in construction.

Figure 25:
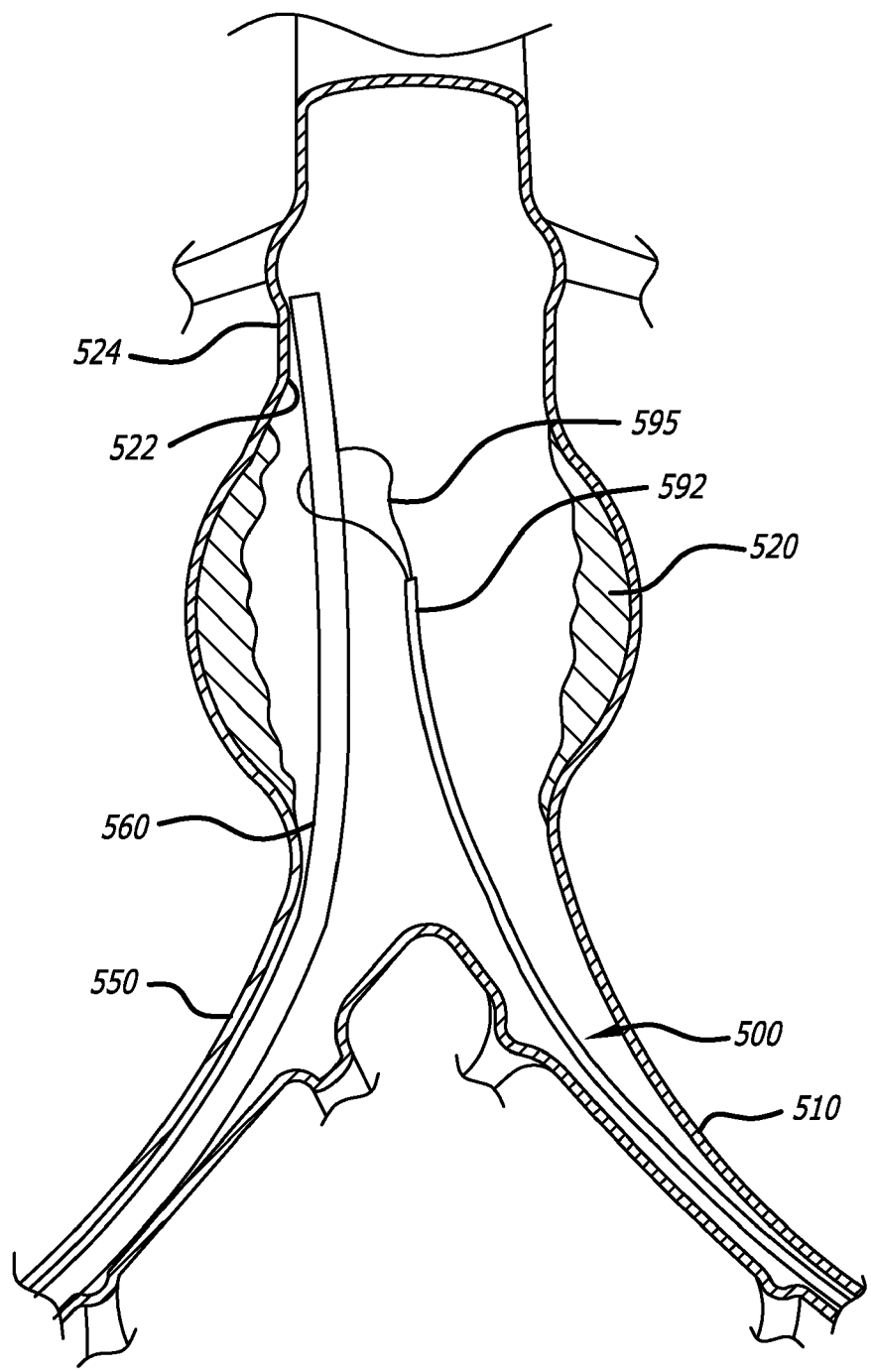
FIG. 25 is a side elevational view, depicting a method of correcting for angulation of the superior anchor stent of a repair device.
Figure 26:
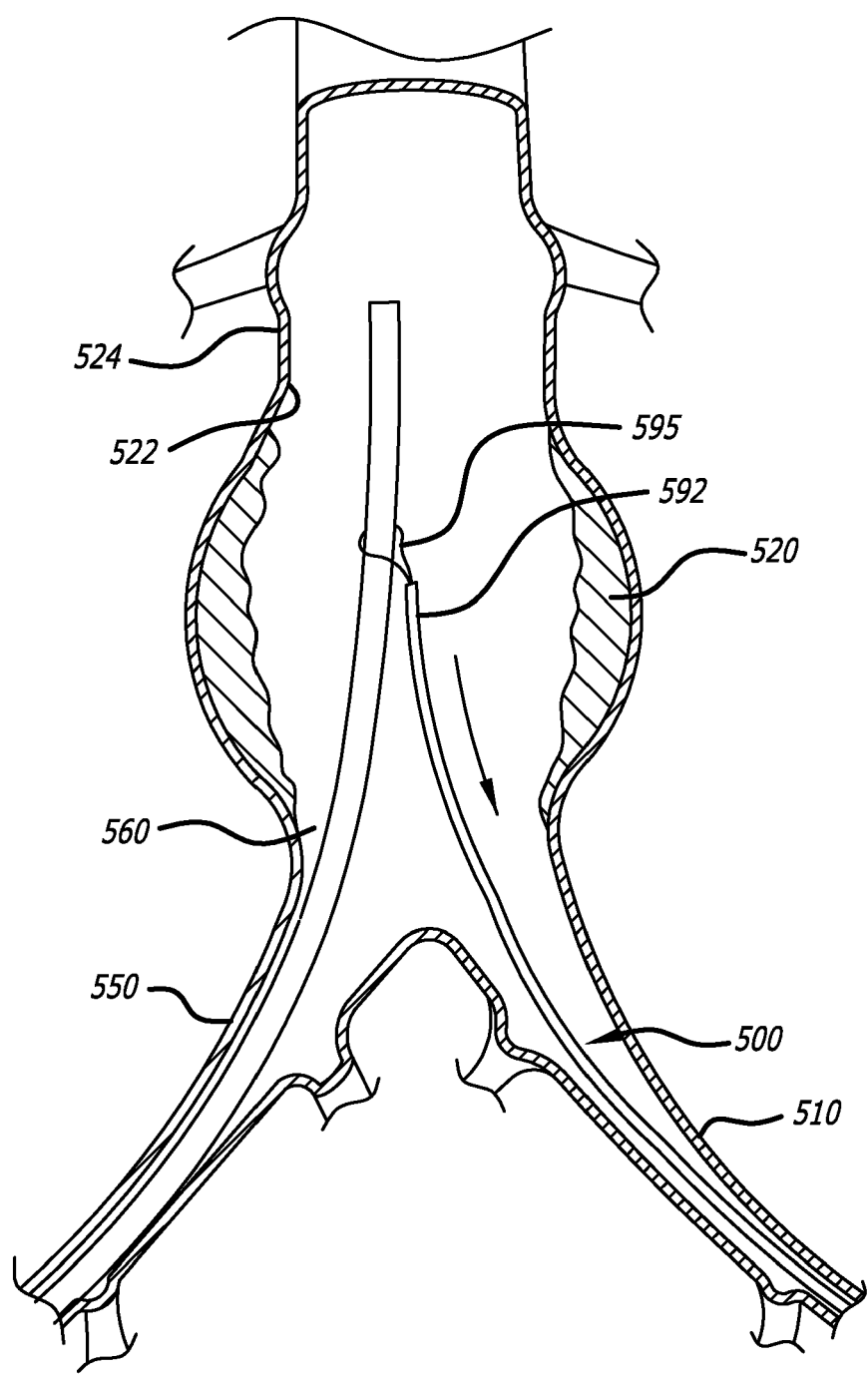
FIG. 26 is a side elevational view, depicting the correction of angulation of the superior anchor stent of a repair device utilizing the method of FIG. 25.

The snare catheter 500 of the present invention may also be utilized to correct for angulation of a superior anchor stent (not shown) of a repair device 570 due to a severely angulated neck in the aorta. As shown in FIGS. 25 and 26, a delivery catheter 560 inserted in the ipsilateral vessel 550 may be up against the wall 522 of the aorta and encounter a great deal of resistance if the neck 524 of the aorta is severely angulated. If the superior anchor stent is released when the delivery catheter 560 is in such a position, the stent may not penetrate the lumen wall on both sides, thereby not properly anchoring the repair device 570.

A snare catheter, inserted in the contralateral vessel 510, may be used by the physician to straighten the delivery catheter 560, thereby correcting for the angulation of the neck 524 prior to deploying the superior anchor stent of the repair device 570. The snare catheter 500 has a housing tube 592 with a capture structure 595 at the superior end. The capture structure 595 may be similar to the wire loop 544 illustrated in FIG. 16, except that the ends are free and lockable, such as with a clip. Alternatively, the capture structure 595 may be a two-part ring similar to forceps in any of the described embodiments. Additionally, aspects of the various embodiments of snares can be combined. It is contemplated that the housing 592 may include a dual or tri-lumen, thereby allowing for a guidewire lumen.

In one method of use, the snare catheter 500 may be inserted into the body through the first or contralateral branch vessel 510 and the capture structure 595, in the form of a wire with free ends, expanded in the main vessel 520. The delivery catheter 560 may then be inserted into the body through the second or ipsilateral branch vessel 550 and through the capture structure 595. The capture structure 595 may then be tightened and the free ends locked together. With the delivery catheter 560 secured to the snare catheter 500, the physician may correct for angulation of the delivery catheter by manipulating the inferior end of the snare catheter, thereby straightening the delivery catheter prior to deploying the superior anchor stent. Once the superior anchor stent is deployed and seated properly in the vessel walls, the free ends of the capture structure 595 are loosened and the wire that embodies the capture structure may be pulled out of the snare catheter 500 to release the delivery catheter 560.

Another method and device contemplated to solve problems associated with in situ assembly departs from the aforementioned methods and devices in that a snare catheter is inserted into a first port of the repair device in order to snare a guidewire inserted into the second branch vessel. The snare catheter is part of a first catheter inserted into the first branch vessel and the guidewire inserted into the second branch vessel is snared and brought into a second port of the repair device. A second catheter may then be inserted into the second branch vessel over the guidewire in order to deploy a limb within the second port of the repair device.

Figure 27:
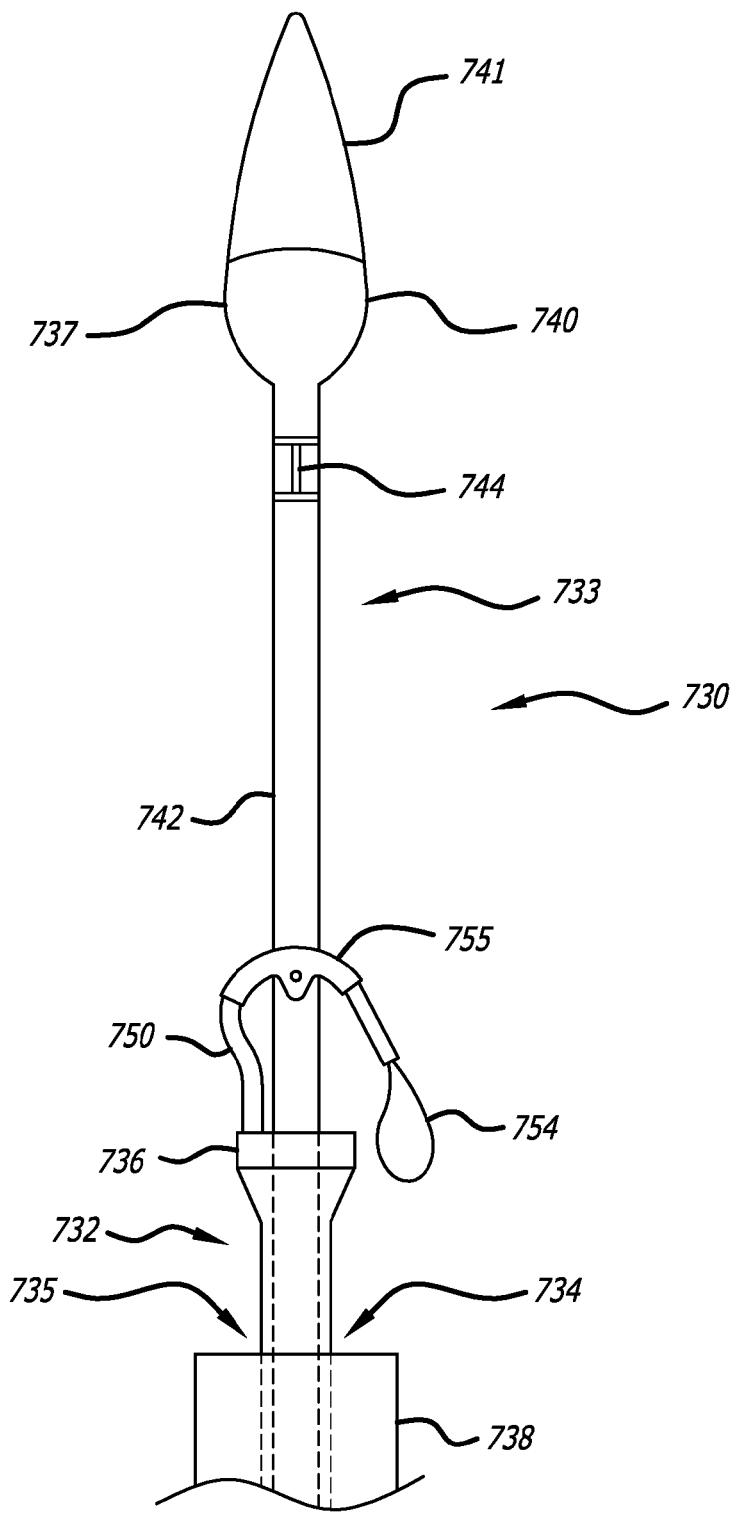
FIG. 27 is a partial side view, depicting a main catheter equipped with a snare catheter and swiveling guide.

Referring now to FIGS. 27–33, a device and a method are described for accomplishing the cannulating of a contralateral opening of a modular abdominal aortic aneurysm endovascular graft implant utilizing a snare catheter inserted from the ipsilateral side. The disclosed system can be used anywhere in a patient's vasculature for the assembly of any repair device by altering the dimensions thereof. As shown in FIG. 27, a repair system 730 includes an elongate main catheter 732 having an inferior portion (not shown) and a superior portion 736. The main catheter further includes a multi-lumen inner catheter 733 having an inferior portion (not shown) and a superior portion 737. The repair system 730 has a tubular jacket 738 which is sized to slide over the main catheter 732 and implant (not shown). The jacket 738 (shown retracted) is used to provide the system 730 with a profile suitable for advancement within vasculature. At a repair site, the jacket 738 is retracted to expose the superior portion 737 of the inner catheter 733, the various components thereof, and a first modular component (shown deployed in FIG. 30).

The superior portion 737 of the inner catheter 733 includes a terminal end configured with a tapered nosecone 741 and a generally blunt jacket guard 740 which mates with the jacket 738 when the system 730 is assembled for advancement through vasculature. The jacket guard 740, tapered nosecone 741 and jacket 738 define an atraumatic superior end. The inner catheter 733 further includes a repair device or modular endovascular graft mounting or receiving portion 742 as well as a release wire port 744. The release wire port 744 is designed to provide an opening for a release wire (not shown) that can be configured to maintain a repair device (or implant) on the inner catheter 733 in a compressed condition upon jacket retraction, then subsequently released to allow the repair device to expand and seal. The system 730 can also be equipped with an expandable member such as a balloon (not shown).

The delivery system 730 further includes a snare lumen 750 and a pivot guide 755. The pivot guide 755 is located on the inner catheter 733 between main catheter 736 and release wire port 744. The pivot guide 755 receives the snare lumen 750 and guides it over a broad curve such that the snare catheter may be directed from the ipsilateral port 63 of the implanted repair device 60 over the bifurcation 64 and out the contralateral port 66.

The snare lumen 750 has a first end (not shown) that extends from outside the patient at the inferior portion of the main catheter 732 and may be advanced in the superior direction such that a second end 751 extends out of the superior portion 736 of the main catheter. The snare lumen 750 may be located in the gap between the main catheter 732 and inner catheter 733 and is configured to slideably receive a snare 754. In a preferred embodiment, the main catheter 732 is a dual lumen catheter, thereby providing a main port for the inner catheter 733 and a second port for the snare lumen 750.

Figure 28:
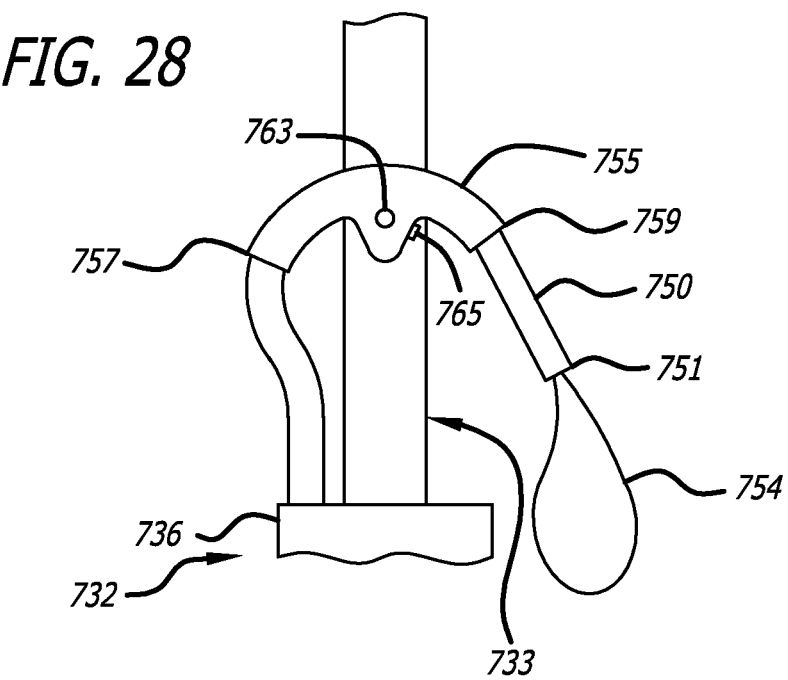
FIG. 28 is a partial side view, depicting the swiveling guide shown in FIG. 27 rotated clockwise by the snare catheter.
Figure 29:
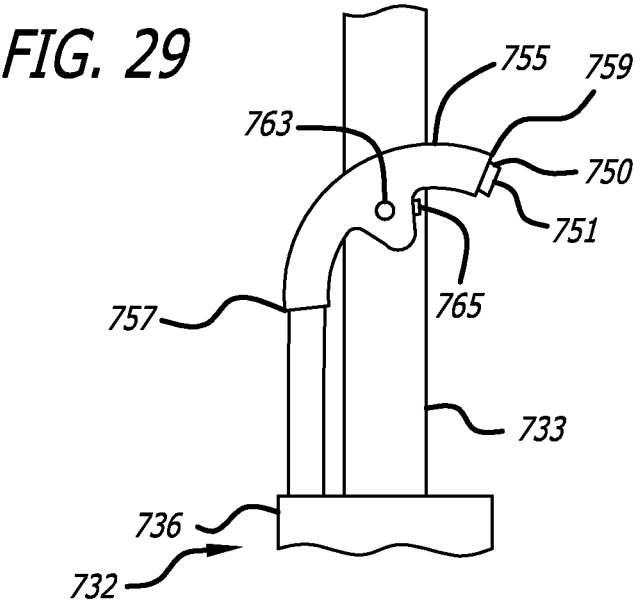
FIG. 29 is a partial side view, depicting the swiveling guide shown in FIG. 27 rotated counter-clockwise by the snare catheter.
Figure 30:
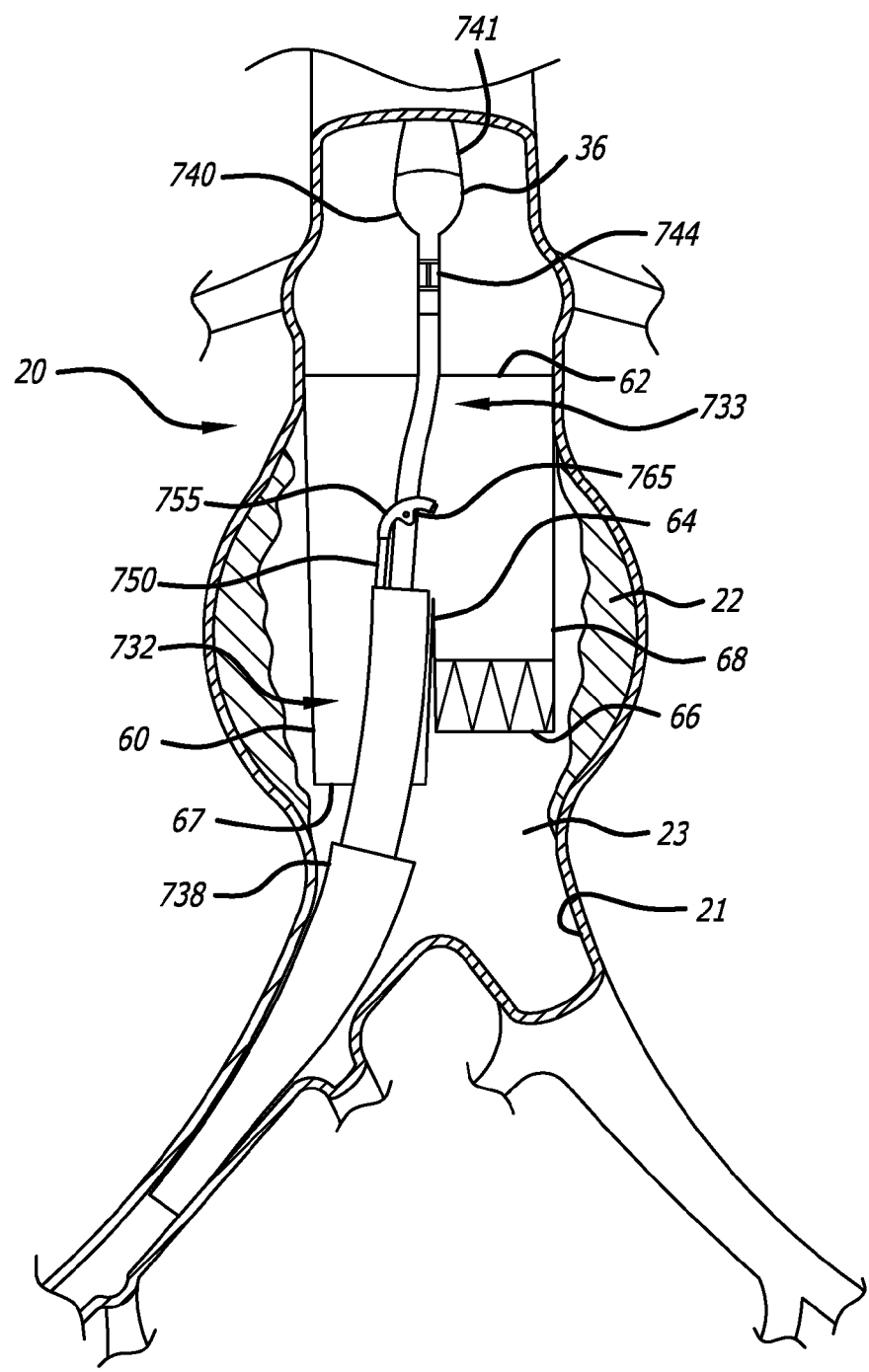
FIG. 30 is a partial cross-sectional side view, depicting the main catheter of FIG. 27 inside a repair device deployed within vasculature, the repair device shown as transparent.

As illustrated in greater detail in FIGS. 28 and 29, the pivot guide 755 is attached to the inner catheter 733 at a pivot point 763 and may be rotated (or oriented) from a substantially parallel position to a substantially perpendicular position relative to the inner catheter 733. A stop 765 limits the rotation of the swiveling guide 755.

In operation, the swiveling guide 755, preferably in the shape of an elbow, facilitates sliding the second end 751 of the snare lumen 750 into the first end 757 of the swiveling guide such that it extends therethrough and protrudes out the second end 759 of the swiveling guide. However, the swiveling guide 755 and snare lumen 750 are also adapted such that the swiveling guide 755 restrains the second end 751 of the snare lumen 750 from being retracted completely therefrom once the snare catheter is inserted. In this way, the snare lumen 750 acts upon the swiveling guide 755 to control the relative position of the swiveling guide with respect to the inner catheter 733 once it is inserted therethrough.

It is contemplated that the second end 751 of the snare lumen 750 may have a taper or a localized narrowing in diameter and the swiveling guide may be formed from a material that allows the second end of the snare catheter to be easily inserted into the first end 757 of the swiveling guide and advanced therethrough while restraining the snare lumen from being retracted in the inferior direction and completely back out of the first end of the swiveling guide. It is further contemplated that the swiveling guide 755 may be adapted such that the second end 751 of the snare lumen 750 may be retracted inside the second end 759 of the swiveling guide but not out the first end 757. The snare lumen 750 may also have a second localized expanding or funneling in diameter (not shown) at an inferior position such that when the snare lumen is inserted into the swiveling guide 755, the second localized rise in diameter acts upon the first end 757 of the swiveling guide to rotate it in a clockwise direction.

Turning now to FIGS. 30–33, a method utilizing the repair system 730 is described. It is contemplated that the repair system 730 may be adapted to use "off the shelf" snare catheters having dimensions from 3 Fr. to 12 Fr.

In a typical implant scenario, the delivery system 730 carrying a first endovascular component repair device 60 is advanced within vasculature to a repair site 22 and the jacket 738 is withdrawn far enough for the superior end 62 of the repair device to be deployed and both the contralateral port 66 and ipsilateral port 67 of the repair device 60 to open. The superior end 62 of the repair device 60 may be self-expanding upon withdrawing a release wire (not shown) or expanded by a balloon (not shown) to thereby be implanted in the region of the repair site 22. In the delivery configuration, the snare lumen 750 is retracted in the inferior direction and the swiveling guide 755 is substantially parallel to the inner catheter 733.

Figure 31:
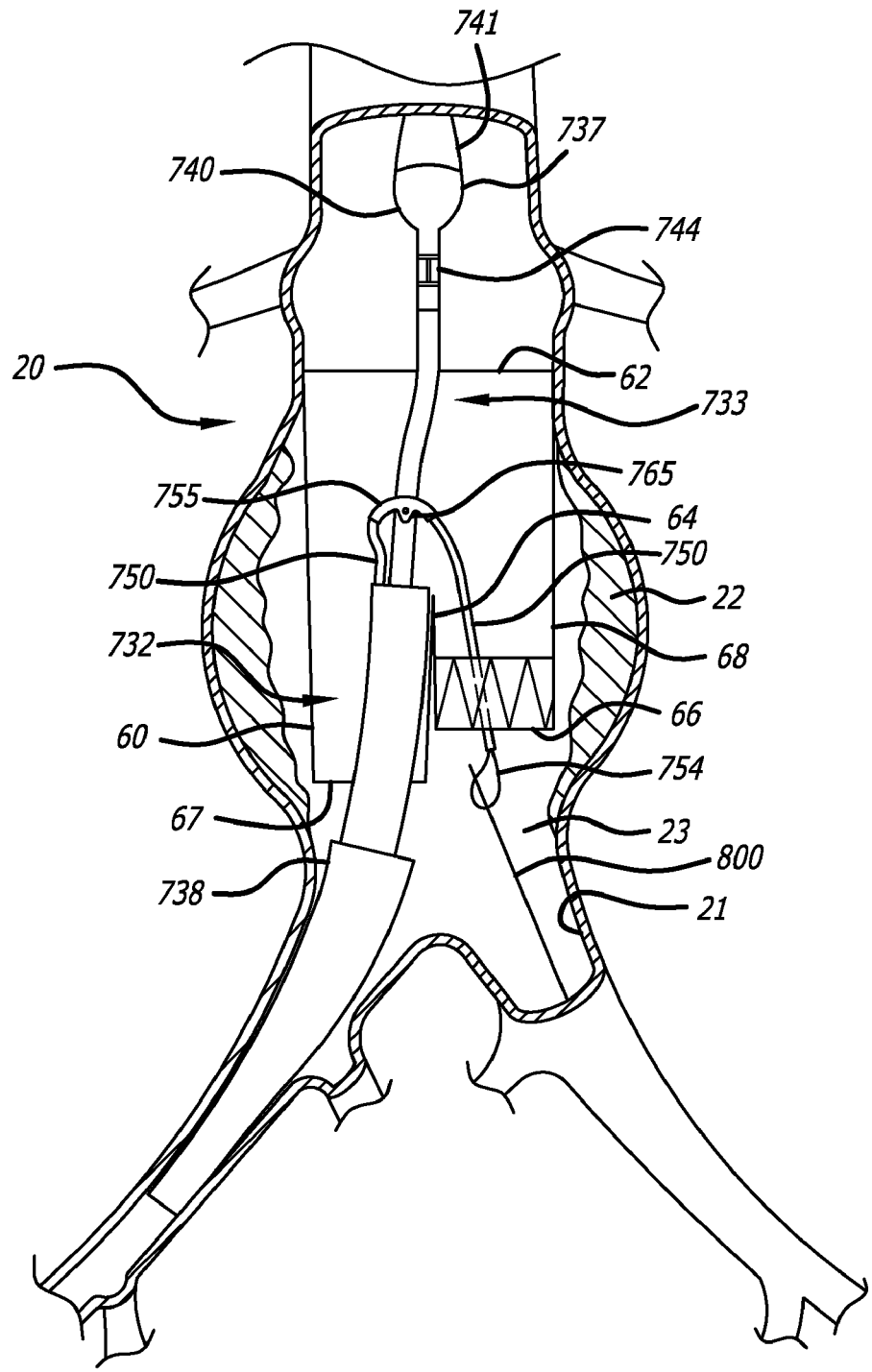
FIG. 31 is a partial cross-sectional view, depicting the assembly of FIG. 30 in which the snare catheter has been advanced through the swiveling guide to capture a guidewire inserted into the contralateral vessel.

The snare lumen 750 is then advanced in the superior direction and through the swiveling guide 755 as illustrated in FIG. 31. The snare lumen 750 causes the swiveling guide 755 to rotate clockwise until the stop 765 prevents further rotation. In this configuration, the swiveling guide 755 is substantially perpendicular to the inner catheter 733 and causes the snare lumen 750 to be advanced over the bifurcation 64 of the repair device 60 and out the contralateral port 66.

With further reference to FIG. 31, a guidewire 800 is then advanced through the contralateral iliac vessel 21 and the snare 754 is advanced out of the snare lumen 750. The snare 754 captures the guidewire 800.

Figure 32:
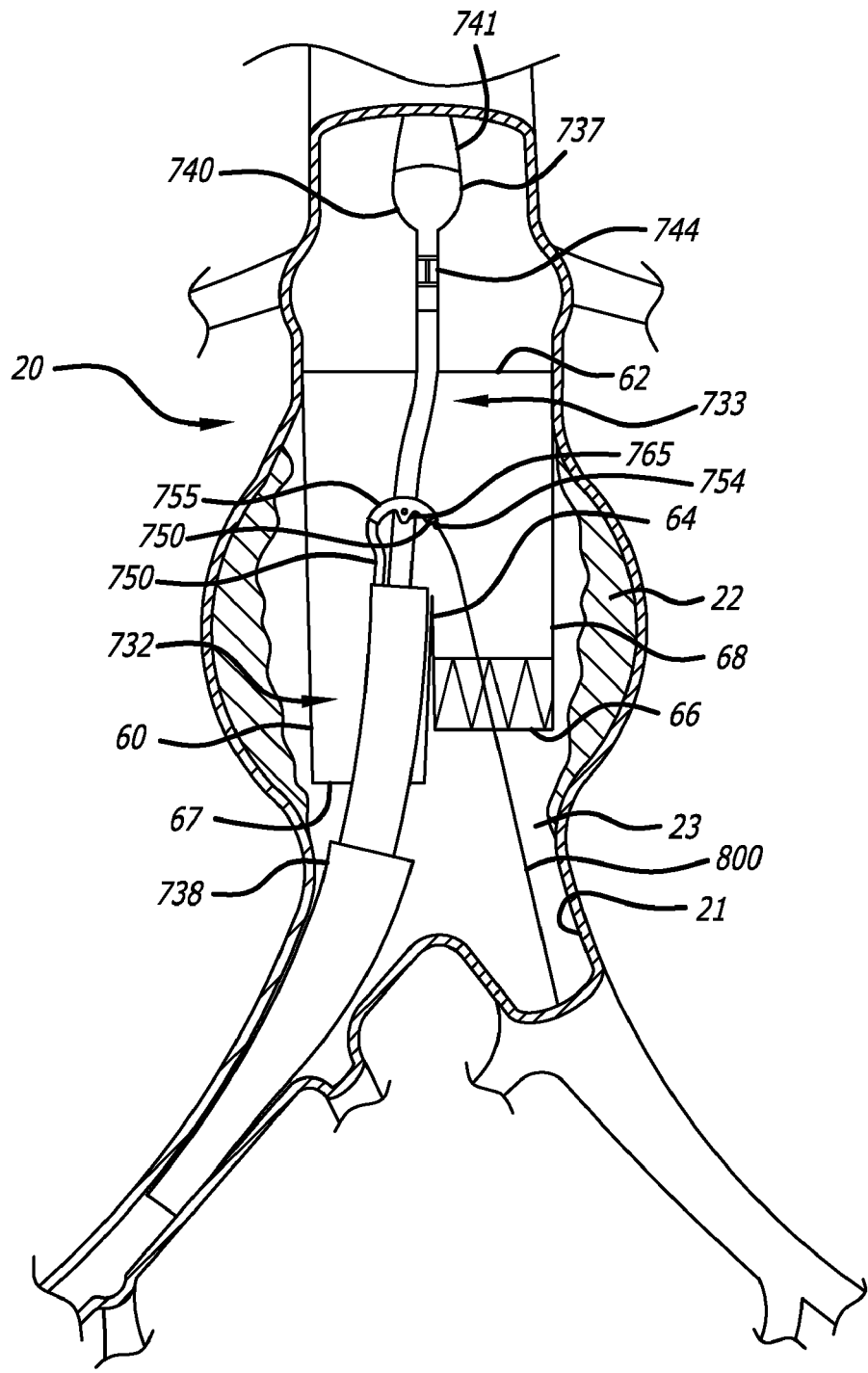
FIG. 32 is a partial cross-sectional view, depicting the assembly of FIG. 30 in which the snare catheter has been retracted into the swiveling guide with the captured guidewire.

The snare lumen 750 is then retracted in the inferior direction, as shown in FIG. 32, such that it pulls the guidewire 800 into the contralateral port 66 of the repair device 60. In this configuration, further movement is restrained by the swiveling guide 755. The snare lumen 750 may have a marking on the inferior portion that protrudes outside the patient at the inferior portion of the main catheter 732 such that the physician can determine when the snare catheter has been advanced to the point where the swiveling guide 755 restrains further movement in the inferior direction. Alternately, the physician may retract the snare catheter until he feels increased resistance to further movement. Furthermore, it is contemplated that the snare lumen 750 second end 751 and swiveling guide 755 second end 759 may have radiopaque markers such that their relative locations may be detected under fluoroscopy.

Once the snare lumen 750 has been advanced in the inferior direction such that further movement is restrained by the swiveling guide 755, the snare catheter will operate on the swiveling guide such that the swiveling guide pivots counter-clockwise until the stop 765 prevents further rotation. In this configuration, the swiveling guide 755 is again substantially parallel to the inner catheter 733, similar to the configuration illustrated in FIG. 30. The snare lumen 750 is then fixed to the inner catheter 733 shaft by a mechanism at the inferior end of the inner catheter (not shown). If desired, the inner catheter 733 and snare lumen 750 may be retracted in the superior direction in order to pull the guidewire 800 across the bifurcation 64 of the repair device 60. Once the guidewire 800 is positioned as desired, the snare 754 is released.

Figure 33:
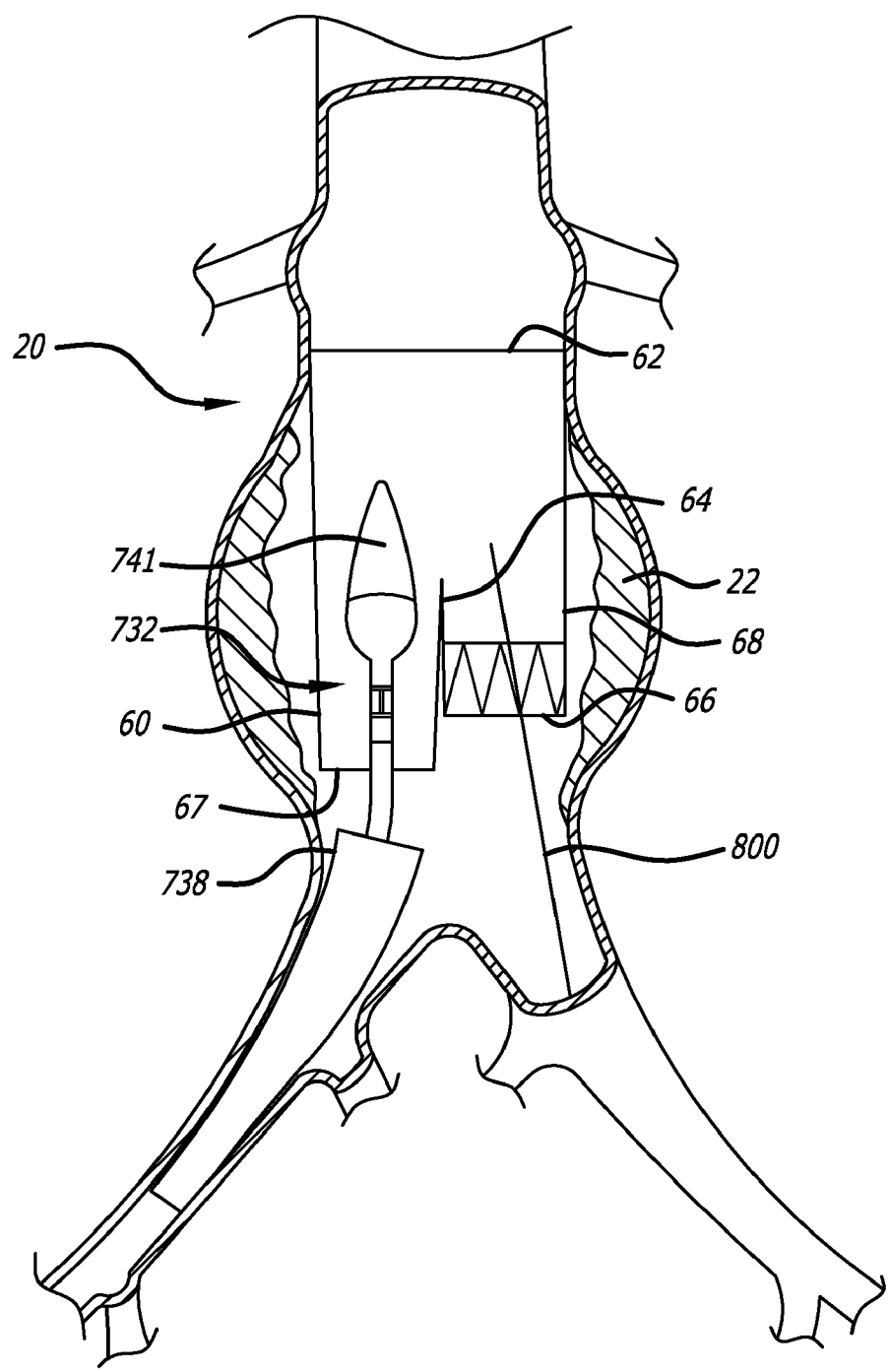
FIG. 33 is a partial cross-sectional view, depicting the assembly of FIG. 30 in which the snare has been released from the guidewire and the snare catheter retracted into the main catheter.

With the swiveling guide 755 substantially parallel to the inner catheter 733 and the snare lumen 750 fixed to the inner catheter, the inner catheter may be retracted into the main catheter 732 as illustrated in FIG. 33. The substantially parallel position of the swiveling guide 755 facilitates removal of the inner catheter from the repair device 60 through the ipsilateral port 67. Deployment of the contralateral limb utilizing a catheter inserted into the contralateral vessel over the guidewire 800 may then be accomplished by methods known in the art.

It is contemplated that the repair system 730 may be utilized in any surgical procedure where it is desired to insert a snare catheter into a vessel and have the snare catheter guided over a broad curve such that it faces the direction of the physician while maintaining control of the location of the inferior end of the snare catheter.

Thus, it will be apparent from the foregoing that, while particular forms of the invention have been illustrated and described, various modifications can be made without departing from the spirit and scope of the invention. For example, the repair device can take on any contemplated form and the disclosed systems can be used to assemble components or hit targets in any area of vasculature. Accordingly, it is not intended that the invention be limited, except as by the appended claims.

What is claimed is:

1. An apparatus for repair of vasculature, comprising:
   a first elongate member having a superior end and an inferior end;
   a second elongate member having a superior end and an inferior end and coaxially slideably disposed within the first elongate member such that the second elongate member may be moved longitudinally with respect to the first elongate member;
   a swiveling guide pivotally attached to the second elongate member, the swiveling guide having a first end and a second end with an aperture therethrough; and
   a snare catheter having a first end and a second end and slideably disposed within the first elongate member such that the snare catheter may be moved longitudinally with respect to the first elongate member, the snare catheter adapted to be inserted into the swiveling guide aperture and moved therethrough such that the second end of the snare catheter protrudes from the second end of the swiveling guide.

2. The apparatus of claim 1, wherein the first elongate member has a dual lumen.

3. The apparatus of claim 1, wherein the swiveling guide is elbow shaped.

4. The apparatus of claim 1, further comprising a means of resisting retraction of the snare catheter completely from the swiveling guide once it is inserted therethrough.

5. The apparatus of claim 4, wherein the means of resisting comprises a tapered second end of the snare catheter.

6. The apparatus of claim 4, wherein the means of resisting comprises a localized increase in diameter near the second end of the snare catheter.

7. The apparatus of claim 4, wherein the means of resisting comprises forming the swiveling guide of a material that facilitates sliding the snare catheter therethrough and resists retracting the snare catheter therefrom.

8. The apparatus of claim 4, wherein the second end of the snare catheter is adapted to be retracted into the swiveling guide after being inserted therethrough.

9. The apparatus of claim 1, wherein the snare catheter is adapted to cause the swiveling guide to rotate in a clockwise direction when moved longitudinally in the superior direction with respect to the first elongate member and to cause the swiveling guide to rotate in a counter-clockwise direction when moved longitudinally in the inferior direction with respect to the first elongate member.

10. The apparatus of claim 1, further comprising a stop attached to the second elongate member, the stop adapted to limit the rotation of the swiveling guide.

11. The apparatus of claim 10, wherein the clockwise and counter-clockwise rotation of the swiveling guide is limited to between a substantially parallel position with respect to the second elongate member and a substantially perpendicular position with respect to the second elongate member.

12. The apparatus of claim 1, further comprising means for releasably attaching the snare catheter to the inferior end of the second elongate member.

13. The apparatus of claim 1, wherein the second elongate member includes an expandable member.

14. The apparatus of claim 1, wherein the second elongate member is configured to carry a repair device.

15. The apparatus of claim 1, wherein the snare catheter has a localized increase in diameter between the first end and the second end that does not enter the swiveling guide.

16. The apparatus of claim 1, wherein the snare catheter has a marker at the first end, the marker indicating when the snare catheter second end is fully retracted such that it is aligned with the swiveling guide second end.

17. The apparatus of claim 1, wherein the snare catheter second end and swiveling guide second end have radiopaque markers.

* * * * *